(12) United States Patent
Bartolozzi et al.

(10) Patent No.: US 9,315,454 B2
(45) Date of Patent: Apr. 19, 2016

(54) COMPOUNDS WHICH MODULATE THE CB2 RECEPTOR

(75) Inventors: Alessandra Bartolozzi, Norwalk, CT (US); Angela Berry, Gaylordsville, CT (US); Doris Riether, Biberach an der Riss (DE); Monika Ermann, Wantage (GB); James Edward Jenkins, Hungerford (GB); Innocent Mushi, Abingdon (GB)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 290 days.

(21) Appl. No.: 13/521,246

(22) PCT Filed: Jan. 11, 2011

(86) PCT No.: PCT/US2011/020767
§ 371 (c)(1),
(2), (4) Date: Aug. 14, 2012

(87) PCT Pub. No.: WO2011/088015
PCT Pub. Date: Jul. 21, 2011

(65) Prior Publication Data
US 2012/0316173 A1    Dec. 13, 2012

Related U.S. Application Data

(60) Provisional application No. 61/295,201, filed on Jan. 15, 2010.

(51) Int. Cl.
| C07C 317/06 | (2006.01) |
| C07C 323/41 | (2006.01) |
| C07C 317/44 | (2006.01) |
| C07D 211/54 | (2006.01) |
| C07D 213/40 | (2006.01) |
| C07D 261/08 | (2006.01) |
| C07D 265/30 | (2006.01) |
| C07D 295/185 | (2006.01) |
| C07D 295/205 | (2006.01) |
| C07D 309/04 | (2006.01) |
| C07D 333/20 | (2006.01) |
| C07D 333/38 | (2006.01) |
| C07D 413/12 | (2006.01) |

(52) U.S. Cl.
CPC ............. *C07C 323/41* (2013.01); *C07C 317/44* (2013.01); *C07D 211/54* (2013.01); *C07D 213/40* (2013.01); *C07D 261/08* (2013.01); *C07D 265/30* (2013.01); *C07D 295/185* (2013.01); *C07D 295/205* (2013.01); *C07D 309/04* (2013.01); *C07D 333/20* (2013.01); *C07D 333/38* (2013.01); *C07D 413/12* (2013.01); *C07C 2101/04* (2013.01); *C07C 2101/08* (2013.01); *C07C 2101/14* (2013.01); *C07C 2101/18* (2013.01)

(58) Field of Classification Search
CPC ............................ C07C 317/06; A61K 31/165
USPC .............................. 544/106; 568/31; 514/618
See application file for complete search history.

(56) References Cited

U.S. PATENT DOCUMENTS

| 3,116,284 A | 12/1963 | Testa |
| 3,117,128 A | 1/1964 | Mooradian |
| 3,577,462 A | 5/1971 | Bruce et al. |
| 3,794,652 A | 2/1974 | Naito |
| 3,966,809 A | 6/1976 | Baker et al. |
| 4,257,954 A | 3/1981 | Schmidt et al. |
| 4,535,087 A | 8/1985 | Spatz |
| 4,672,065 A | 6/1987 | Spatz |
| 4,734,125 A | 3/1988 | Gehring et al. |
| 4,859,707 A | 8/1989 | Loftsson et al. |
| 5,256,658 A | 10/1993 | Hsi et al. |
| 5,428,037 A | 6/1995 | Pascal et al. |
| 5,475,130 A | 12/1995 | Sato et al. |
| 5,491,170 A | 2/1996 | Lee et al. |

(Continued)

FOREIGN PATENT DOCUMENTS

| CH | 312963 A | 3/1956 |
| DE | 1080563 B | 12/1957 |

(Continued)

OTHER PUBLICATIONS

STN results for Dorme et al., Bulletin de la Societe Chimique de France (1959), (9), 2582-8.*

(Continued)

*Primary Examiner* — Yong Chu
*Assistant Examiner* — Sonya Wright
(74) *Attorney, Agent, or Firm* — Michael P. Morris; Atabak R. Royaee

(57) ABSTRACT

Compounds of formula (I) are disclosed. Compounds according to the invention bind to and are agonists, antagonists or inverse agonists of the CB2 receptor, and are useful for treating inflammation. Those compounds which are agonists are additionally useful for treating pain.

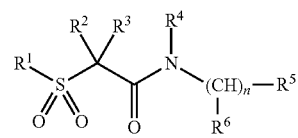

(I)

12 Claims, No Drawings

(56) References Cited

U.S. PATENT DOCUMENTS

| | | | |
|---|---|---|---|
| 5,571,921 | A | 11/1996 | Bender et al. |
| 5,583,147 | A | 12/1996 | Ko et al. |
| 5,656,634 | A | 8/1997 | Chang et al. |
| 5,834,490 | A | 11/1998 | Verde-Casanova et al. |
| 5,847,153 | A | 12/1998 | Warpehoski et al. |
| 5,958,940 | A | 9/1999 | Rane et al. |
| 5,968,929 | A | 10/1999 | Blythin et al. |
| 6,057,371 | A | 5/2000 | Glennon |
| 6,176,442 | B1 | 1/2001 | Eicher et al. |
| 6,221,866 | B1 | 4/2001 | Brendel et al. |
| 6,355,653 | B1 | 3/2002 | Trottmann et al. |
| 6,359,009 | B1 | 3/2002 | Diehl et al. |
| 6,410,792 | B1 | 6/2002 | Connell et al. |
| 6,414,011 | B1 | 7/2002 | Hogenkamp et al. |
| 6,437,177 | B1 | 8/2002 | Warpehoski et al. |
| 6,453,795 | B1 | 9/2002 | Eicher et al. |
| 6,528,529 | B1 | 3/2003 | Brann et al. |
| 6,573,278 | B2 | 6/2003 | Mittendorf et al. |
| 6,610,711 | B2 | 8/2003 | Armer et al. |
| 6,737,418 | B2 | 5/2004 | Hogenkamp et al. |
| 6,756,404 | B2 | 6/2004 | Livinghouse |
| 6,930,115 | B2 | 8/2005 | Fujii et al. |
| 7,476,756 | B2 | 1/2009 | Almario-Garcia et al. |
| 7,585,881 | B2 | 9/2009 | Edwards et al. |
| 7,595,397 | B2 | 9/2009 | Zindell et al. |
| 7,776,897 | B2 | 8/2010 | Murakami et al. |
| 7,928,123 | B2 | 4/2011 | Berry et al. |
| 7,935,715 | B2 | 5/2011 | Berry et al. |
| 8,048,899 | B2 | 11/2011 | Bartolozzi et al. |
| 8,173,638 | B2 | 5/2012 | Berry et al. |
| 8,178,568 | B2 | 5/2012 | Regan et al. |
| 8,299,103 | B2 | 10/2012 | Bartolozzi et al. |
| 8,299,111 | B2 * | 10/2012 | Berry et al. ............ 514/406 |
| 8,329,735 | B2 | 12/2012 | Ermann et al. |
| 8,362,039 | B2 | 1/2013 | Bartolozzi et al. |
| 8,546,563 | B2 | 10/2013 | Berry et al. |
| 2002/0099035 | A1 | 7/2002 | Sandanayaka et al. |
| 2004/0067999 | A1 | 4/2004 | Block et al. |
| 2004/0152747 | A1 | 8/2004 | Chen et al. |
| 2004/0242666 | A1 | 12/2004 | Chen |
| 2004/0242913 | A1 | 12/2004 | Ducray et al. |
| 2005/0059663 | A1 | 3/2005 | Martin et al. |
| 2005/0182108 | A1 | 8/2005 | Carson et al. |
| 2005/0222219 | A1 | 10/2005 | Chen |
| 2006/0009491 | A1 | 1/2006 | Yao et al. |
| 2006/0061726 | A1 | 3/2006 | Okuyama |
| 2006/0079557 | A1 | 4/2006 | Dolle et al. |
| 2006/0173022 | A1 | 8/2006 | Schaper |
| 2007/0021403 | A1 | 1/2007 | Abouabdellah et al. |
| 2007/0021430 | A1 | 1/2007 | Chen et al. |
| 2007/0093501 | A1 | 4/2007 | Kubo et al. |
| 2007/0179126 | A1 | 8/2007 | Casellas et al. |
| 2007/0191340 | A1 | 8/2007 | Zindell et al. |
| 2007/0213311 | A1 | 9/2007 | Li et al. |
| 2007/0270426 | A1 | 11/2007 | Chen |
| 2008/0039464 | A1 | 2/2008 | Berry et al. |
| 2008/0064690 | A1 | 3/2008 | Atkinson et al. |
| 2008/0081342 | A1 | 4/2008 | Fung |
| 2008/0081822 | A1 | 4/2008 | Berry et al. |
| 2008/0227781 | A1 | 9/2008 | Brodney et al. |
| 2009/0163545 | A1 | 6/2009 | Goldfarb |
| 2009/0275611 | A1 | 11/2009 | Riether et al. |
| 2010/0009964 | A1 | 1/2010 | Berry et al. |
| 2010/0029644 | A1 | 2/2010 | Riether et al. |
| 2010/0076029 | A1 | 3/2010 | Bartolozzi et al. |
| 2010/0081644 | A1 | 4/2010 | Bartolozzi et al. |
| 2010/0261708 | A1 | 10/2010 | Cirillo et al. |
| 2010/0333304 | A1 | 12/2010 | Berry et al. |
| 2011/0071127 | A1 | 3/2011 | Berry et al. |
| 2011/0071196 | A1 | 3/2011 | Bartolozzi et al. |
| 2011/0124696 | A1 | 5/2011 | Regan et al. |
| 2011/0130431 | A1 | 6/2011 | Berry et al. |
| 2011/0136869 | A1 | 6/2011 | Bartolozzi et al. |
| 2011/0190256 | A1 | 8/2011 | Cirillo et al. |
| 2011/0312932 | A1 | 12/2011 | Bartolozzi et al. |
| 2011/0312944 | A1 | 12/2011 | Bartolozzi et al. |
| 2012/0010184 | A1 | 1/2012 | Bartolozzi et al. |
| 2012/0015988 | A1 | 1/2012 | Hickey et al. |
| 2012/0071529 | A1 | 3/2012 | Ermann et al. |
| 2012/0142666 | A1 | 6/2012 | Hickey et al. |
| 2012/0142677 | A1 | 6/2012 | Berry et al. |
| 2012/0316173 | A1 | 12/2012 | Bartolozzi et al. |

FOREIGN PATENT DOCUMENTS

| | | | |
|---|---|---|---|
| DE | 3636278 | A1 | 5/1988 |
| EP | 0628555 | | 12/1994 |
| EP | 0929519 | | 7/1999 |
| EP | 0970046 | A1 | 1/2000 |
| EP | 1790641 | A1 | 5/2007 |
| FR | 2866885 | A1 | 9/2005 |
| FR | 2872813 | A1 | 1/2006 |
| GB | 853799 | A | 11/1960 |
| GB | 884258 | A | 12/1961 |
| GB | 1237126 | A | 6/1971 |
| JP | 61-18755 | * | 1/1986 |
| JP | 61027905 | U | 2/1986 |
| JP | 61027955 | A | 2/1986 |
| JP | 61126071 | A | 6/1986 |
| JP | 2003155285 | | 5/2003 |
| JP | 2006504796 | A | 2/2006 |
| JP | 2006143667 | A | 6/2006 |
| JP | 2006525990 | A | 11/2006 |
| JP | 2007502828 | A | 2/2007 |
| JP | 2007530525 | A | 11/2007 |
| JP | 2007530661 | A | 11/2007 |
| WO | 9405628 | | 3/1994 |
| WO | 9407607 | | 4/1994 |
| WO | 9626925 | A1 | 9/1996 |
| WO | 9712683 | | 4/1997 |
| WO | 9712687 | | 4/1997 |
| WO | 9720590 | | 6/1997 |
| WO | 9746556 | | 12/1997 |
| WO | 9808295 | | 2/1998 |
| WO | 9811097 | A1 | 3/1998 |
| WO | 9813340 | | 4/1998 |
| WO | 9838163 | A1 | 9/1998 |
| WO | 9965889 | A1 | 12/1999 |
| WO | 0008015 | A2 | 2/2000 |
| WO | 0100573 | | 1/2001 |
| WO | 0129007 | | 4/2001 |
| WO | 0164651 | | 9/2001 |
| WO | 02051806 | | 7/2002 |
| WO | 02088089 | A1 | 7/2002 |
| WO | 02062750 | | 8/2002 |
| WO | 03037274 | A2 | 5/2003 |
| WO | 03055482 | | 7/2003 |
| WO | 03074493 | A1 | 9/2003 |
| WO | 2004000807 | | 12/2003 |
| WO | 2004014370 | A2 | 2/2004 |
| WO | 2004014825 | | 2/2004 |
| WO | 2004014902 | A2 | 2/2004 |
| WO | 2004018433 | | 3/2004 |
| WO | 2004026301 | A1 | 4/2004 |
| WO | 2004029027 | | 4/2004 |
| WO | 2004042351 | A2 | 5/2004 |
| WO | 2004050643 | | 6/2004 |
| WO | 2004060882 | | 7/2004 |
| WO | 2004099200 | A1 | 11/2004 |
| WO | 2004099205 | | 11/2004 |
| WO | 2005027837 | | 3/2005 |
| WO | 2005040355 | | 5/2005 |
| WO | 2005044797 | A1 | 5/2005 |
| WO | 2005068448 | A1 | 7/2005 |
| WO | 2005077345 | A1 | 8/2005 |
| WO | 2005077368 | A2 | 8/2005 |
| WO | 2005077373 | A2 | 8/2005 |
| WO | 2005085227 | | 9/2005 |
| WO | 2006000031 | A1 | 1/2006 |
| WO | 2006012227 | | 2/2006 |
| WO | 2006030805 | A1 | 3/2006 |
| WO | 2006060461 | | 6/2006 |
| WO | 2006074445 | A2 | 7/2006 |
| WO | 2006080040 | | 8/2006 |

(56) References Cited

FOREIGN PATENT DOCUMENTS

| WO | 2006095159 | | 9/2006 |
|---|---|---|---|
| WO | 2006100502 | | 9/2006 |
| WO | 2006117461 | A2 | 11/2006 |
| WO | 2007020502 | A2 | 2/2007 |
| WO | 2007054770 | A2 | 5/2007 |
| WO | 2007070760 | A2 | 6/2007 |
| WO | 2007080382 | A1 | 7/2007 |
| WO | 2007102059 | | 9/2007 |
| WO | 2007118041 | A1 | 10/2007 |
| WO | 2007140385 | A2 | 12/2007 |
| WO | 2008014199 | A2 | 1/2008 |
| WO | WO-2008014199 | * | 1/2008 |
| WO | 2008023159 | A1 | 2/2008 |
| WO | 2008039645 | A1 | 4/2008 |
| WO | 2008048914 | A1 | 4/2008 |
| WO | 2008064054 | A2 | 5/2008 |
| WO | 2008098025 | A1 | 8/2008 |
| WO | 2008104994 | A2 | 9/2008 |
| WO | 2009055357 | A1 | 4/2009 |
| WO | 2009061652 | A1 | 5/2009 |
| WO | 2009077533 | A1 | 6/2009 |
| WO | 2009086303 | A2 | 7/2009 |
| WO | 2009105509 | A1 | 8/2009 |
| WO | 2009140089 | A2 | 11/2009 |
| WO | 2010005782 | A1 | 1/2010 |
| WO | 2010036630 | A2 | 4/2010 |
| WO | 2010036631 | A2 | 4/2010 |
| WO | 2010077836 | A2 | 7/2010 |
| WO | 2010096371 | A2 | 8/2010 |
| WO | 2010147791 | A1 | 12/2010 |
| WO | 2010147792 | A2 | 12/2010 |
| WO | 2011035159 | A1 | 3/2011 |
| WO | 2011037795 | | 3/2011 |
| WO | 2011088015 | A1 | 7/2011 |
| WO | 2011109324 | A1 | 9/2011 |
| WO | 2012012307 | A1 | 1/2012 |

OTHER PUBLICATIONS

International Search Report and Written Opinion for PCT/US2011/020767 mailed Jun. 22, 2011.
Marx, I. E. et al., "Discovery of a-amidosulfones as potent and selective agonists of CB2: Synthesis, SAR, and pharmacokinetic properties". Bioorganic and Medicinal Chemistry Letters, 2009, p. 31-35.
White, J.D. et al., "Conversion of Carbamates to Amidosulphones and Amides. Synthesis of the [ 14 C]—Labeled Antiobestity Agent Ro23-7637", Organice Letters, vol. 4. No. 10, Apr. 17, 2002, pp. 1803-1806.
LeBerre, A. et al., No. 150—Alpha-sulfocarboxylic acids and derivatives. V.-Acyclic sulfamoyl carboxyesters and carboxamides. 1,2-Thiazetidine 3-one 1,1-dioxides. National Conservatory of Skills and Trades, Laborator of Industrial Chemistry. Manuscript recieved Sep. 17, 1974, p. 807-811.
Abstract in English for DE 3636278, May 5, 1988.
Abstract in English for JP 2006-143667, Jun. 8, 2006.
Caplus—1967:454417, Kunieda et al., Chemical Pharmaceutical Bulletin, vol. 15, No. 3, 1967.
Catalano, A. et al., "Constrained analogues of tocainide as potent skeletal muscle sodium channel blockers toward the development of antimyotonic agents". European Journal of Medicinal Chemistry, vol. 43, No. 11, 2008, p. 2535-2540.
Database Pubchem Substance, 2005, Retrieved online from <http://www.ncbi.nlm.nih.gov/pcsubstance>.
Dorme, R. et al., "Synthesis and Properties of Novel Dimethoxy-6,7 dihydro-3,4- or Tetrahydro-1,2,3,4-isoquinolines." Societe Chimique de France, 1959, No. 9, pp. 2582-2587.
Hauske, J. et al., "Design and Synthesis of Novel FKBP Inhibitors." Journal of Medicinal Chemistry, 1992, vol. 35, No. 23, pp. 4284-4296.
Ho, B. et al., "Synthesis and structure-activity relationships of potential anticonvulsants based on 2-piperidinecarboxylic acid and related pharmacophores." European Journal of Medicial Chemistry, 2001, vol. 36, No. 3, pp. 265-286.

International Search Report and Written Opinion for PCT/EP2014/060033 mailed Jul. 3, 2014.
Iwakubo, M. et al., "Design and synthesis of Rho kinase inhibitors (II)". Biorganic and Medicinal Chemistry, Vo. 15, No. 1, Nov. 15, 2006, p. 350-364.
Kulkarni, S.S. et al., "Design and synthesis of noncompetitive metabotropic glutamate receptor subtype 5 antagonists." Bioorganic and Medicinal Chemistry Letters, Vo. 16, No. 13, Jul. 1, 2006, p. 3371-3375.
Li, S. et al., "The Synthesis and Preliminary Activity Assay In Vitro of Peptide-like Derivatives as APN Inhibitors." Archives of Pharmacal Research, 2008, vol. 31, No. 10, pp. 1231-1239.
Silverman, Richard B., The Organic Chemistry of Drug Design and Drug Action, 2nd Edition, 2004, Elsevier, pp. 29-34.
Stalberg, O. et al. "Capillary Electrophoretic Separation of Basic Drugs Using Surface-Modified C8 Capillaries and Derivatized Cyclodextrins as Structural/Chiral Selectors." Chromatographia, 1995, vol. 40, No. 11/12, pp. 697-704.
Wei, Ling et al., "Solid-Phase Synthesis of FKBP12 Inhibitors: N-Sulfonyl and N-Carbamoylprolyl/pipecolyl Amides." Bioorganic & Medicinal Chemistry Letters, 2002, vol. 12, No. 10, pp. 1429-1433.
Wermuth, C. G., The Practice of Medicinal Chemistry, 2008, Third Edition, Ch. 17, pp. 363-379.
Abstract in English for JP 61-027905, Feb. 7, 1986, and WO199626925, Sep. 1996, Derwent Abstract.
Abstract in English for JP 61-027955, Feb. 7, 1986, Derwent.
Abstract in English for JP2003155285, May 27, 2003, Inventor: T. Makoto.
Anisimov, A. V. et al., "Synthesis of Sulfonyl and Sulfenyl Derivatives of Pyridine and 1,2,4-Triazole". Russian Journal of Organic Chemistry, 2006, vol. 42, No. 6, pp. 918-921.
Aranapakam, V. et al., "Synthesis and Structure—Activity Relationship of a-Sulfonylhydroxamic Acids as Novel, Orally Active Matrix Metalloproteinase Inhibitors for the treatment of Osteoarthritis", J. Med. Chem., 2003, vol. 46, p. 2361.
Aranapakam, V. et al., "Synthesis and Structure—Activity relationship of n-Substituted 4-Arylsulfonylpiperidine-4-hydroxamic Acids as Novel, Orally Active matrix Metalloproteinase Inhibitors for the treatment of Osteoarthritis", J. Med. Chem., 2003, vol. 46, p. 2376.
Aranapakam, V., et al., "Synthesis and Structure—Activity relationships of 4-alkynyloxy Phenyl Sulfanyl, Sulfinyl, and Sulfonyl Alkyl Hydroxamates as Tumor Necrosis Factor-a Converting Enzyme and Matrix Metalloproteinase Inhibitors", J. Med. Chem., 2004, vol. 47, p. 6255.
Arevalo-Martin, A. et al., "Therapeutic Action of Cannabinoids in a Murine model of Multiple Sclerosis", J. of Neuroscience, 2003, vol. 23, No. 7, p. 2511.
Atwell, G. J. et al., "Relationships between Structure and Kinetics of Cyclization of 2-Aminoaryl Amides: Potential Prodrugs of Cyclization-Activitated Aromatic Mustards"., XP-002465787, J. Med. Chem, 1994, 37, 371-380.
Audouze, K. et al., "New series of morpholine and 1,4-oxazepane derivatives as dopamine D4 receptor ligands. Synthesis and 3D-QSAR model." J. Med. Chem, vol. 47, No. 12, pp. 3089-3104, 2003.
Bair, K. W. et al., "(1-pyrenylmethyl)amino alcohols, a new class of antitumor DNA intercalators. Discovery and intial amine side chain structure-activity studies". Jornal of Medicinal Chemistry, vol. 33, 1990, pp. 2385-2393.
Baker, D. et al., "Cannabinoids control spasticity and tremor in a multiple sclerosis model", Nature, 2000, vol. 404, p. 84.
Baltzly, R. et al., "The preparation of N-mono-substituted and unsymmetrically disubstituted piperzines". Journal of American Chemical Society, vol. 66, 1944, pp. 263-265.
Baltzly,R. et al., "Unsymmetrically substituted piperazines. V. Piperazine ureas". The Journal of the American Chemical Society, vol. 76, 1954, pp. 1165-1166.
Balzarini, J. et al., "Antiretroviral activity of semisynthetic derivatives of glycopeptide antibiotics". J. Med. Chem., 2003, vol. 46, No. 13, pp. 2755-2764.

(56) References Cited

OTHER PUBLICATIONS

Beilstein Database—Beilstein Registry No. 1084348. CAS Registry No. 6125-38-8. Beilstein Institute for Organic Chemistry. 1966, Abstract.
Beilstein Database—Beilstein Registry No. 1179643. CAS Registry No. 54890-73-2. Beilstein Institute for Organic Chemistry. 1974, Abstract.
Beilstein Database—Beilstein Registry No. 5396840. CAS Registry No. 54890-82-3. Beilstein Institute for Organic Chemistry. 1974, Abstract.
Beilstein Database—Beilstein Registry No. 5398283. CAS Registry No. 68558-02-01. Beilstein Institute for Organic Chemistry. 1978, Abstract.
Beilstein Database—Beilstein Registry No. 857451. CAS Registry No. 37901-58-9. Beilstein Institute for Organic Chemistry. 1972, Abstract.
Binisti, C. et al., "Structure-Activity relationships in platelet-activating factor (PAF). 11-From PAF-antagonism to phospholipase A2 inhibition: syntheses and structure-activity relationships in 1-arylsulfamido-2-alkylpiperazines", Eur. J. Med. Chem., 2001, vol. 36, p. 809.
Brown, P. J. et al., "A Ureido-Thioisobutyric Acid (GW9578) Is a Subtype-Selective PPARa Agonist with Potent Lipid-Lowering Activity", J. Med. Chem. 1999, vol. 42, p. 3785.
Bruche, L. et al., "1,3-Dipolar Cycloadditions of 3,5-Dichloro-2,4,6-trimethylbenzonitrile Oxide to Phenylsulfonylallenes". Journal of Organic Chemistry, vol. 50, 1985, pp. 3206-3208, p. 3206, compounds 5a and 5b.
Buckley, N. E. et al., "Immunomodulation by cannabinoids is absent in mice deficient for the cannabinoid CB2 receptor", Eur. J. Pharmacology, 2000, vol. 396, p. 141.
Caplus—1990:497413, Zara-Kaczian, Acta Chimica Hungarica, 1989.
Caplus—RN 112298-90-5 (Tommasi), retrieved from CAPLUS on Jan. 2, 2009.
Caplus—RN 262371-16-4 (Organ), retrieved from CAPLUS on Jan. 2, 2009.
Caplus—RN 57992-82-2 (Babayan), retrieved from CAPLUS on Jan. 2, 2009.
Carenzi, A, et al., "New Isoxazole Derivatives Provided with Antihypertensive Activity". Arzneimittel-Forschung, vol. 39, No. 6, 1989, p. 624-646.
Cartwright, D., et al., "Abnormal Nucleophillic substitution in 3-trichloromethylpyridine, its N-oxide and 3,5-Bis (trichloromethyl)pyridine". Tetrahedron, Elsevier Science Publishers, Amsterdam, vol. 51, No. 47, 1995, pp. 12791-12796.
Chang, M. Y. et al, "Reaction of different a-sulfonyl acetamides with methyl acrylate". Tetrahedron 58 (2002) p. 5075-5080.
Chem Abstract—Accession No. 126:89390, Abstract of JP8311026, Kumaiai Chemical Industry Co., Nov. 26, 1996.
ChemAbstract: 246020-62-2 registry copyright ACS on STN, entered 1999. CHEMCATS.
ChemAbstracts, Ukraine. Order Nos. T6110295, T5962700, T5962703 abstract and "Enamine Screening Library", Jan. 1, 2009, Enamine, 23 Alexandra Matrosova St., 01103 Kiev, Ukraine.
ChemAbstracts: 693218-49-4 and 402562-90-7. 2004.
Chen, D. et al., "Preparation, properties, and synthetic potentials of novel boronates in a flourous version (flourous boronates)". Organic Letters, vol. 4. No. 6, 2002, pp. 1003-1005.
Clark, N. G. et al., "The Fungicidal Activity of Substituted Acetanilides and Related Compounds". Biochemical Journal, 1953, vol. 55, p. 839-851.
Cockcroft, X. L. et al., "Phthalazinones 2: optimization and synthesis of novel potent inhibitors of ply(ADP-ribose) polymerase". Bioorganic & Medicinal Chemistry Letters, 16, 2006, pp. 1040-1044.
Dav, Jr., R. A. et al., "Polarography of phenyl 2-thienyl and 2,2'-dithienyl ketones". 1953.

El-Hawash, S. A. M., et al., "Synthesis and invitro-Anticancer and Antimicrobial Evaluation of Some Novel Quinoxalines Derived from 3-Phenylquinoxaline-2(1H)-thione". Arch. Pharm. Chem. Life Sci, 2006, 339, p. 437-447.
EP Office Action for Case 09-0388 dated Mar. 22, 2010.
Ermann, M. et al., "Arylsulfonamide CB2 receptor agonists: SAR and optimization of CB2 selectivity", Bioorganic and Medicinal Chemistry Letters 18 (2008) 1725-1729.
Ermann, M., et al., Moscone Conv.Ctr. "Discovery of a novel class of CB2 receptor agonists". Presented at the Cambridge Healthcare Institute's 15th International Molecular Medicine Tri-Conference, Moscone Convention Center, San Francisco, CA, USA. Mar. 25-28, 2008.
Ermann, M., et al., UK, "Discovery of a novel class of CB2 receptor agonists". Presented at the 14th SCI-RSC Medicinal Chemistry Symposium, Churchill College, Cambridge, UK, Sep. 23-26, 2007.
Evans, W. J. et al., "A Rearrangement of Carbamyl-sulphones and -sulphides". Journal of the Chemical Society, 1936, p. 329-331.
Faucher, A. M. et al., "Discovery of Small-Molecule Inhibitors of the ATPase Activity of Human Papillomavirus E1 Helicase", J. Med. Chem., 2004, vol. 47, p. 18.
Field, L. et al., "Grignard Reagents of Sulfones. IV. Reactions with Nitriles, Esters and an Isocyanate". Journal of American Society, vol. 78, 1956, p. 4389-4394.
Field, L., et al., "Methyl p-Tolyl Sulfone", Organic Syntheses, Coll. vol. 4, p. 674, 1963; vol. 38, p. 62, (1958).
Fringuelli, F. et al., "Solvent-Free Al(OTi)3-catalyzed aminolysis of 1,2-Epoxides by 2-picolylamine: a key step in the synthesis of ionic liquids". Journal of Organic Chemistry, vol. 69, 2004, pp. 7745-7747.
Gao, M., et al "Synthesis of new carbon-11 labeled benzoxazole derivatives for PET imaging of 5-HT3 receptor", Science Direct, European Journal of Medicinal Chemistry, 43, 2008, pp. 1570-1574.
Gartst, M., et al., "Hydroformylation of bisolefinic amine derivatives catalyzed by cobalt and rhodium". Journal of Organic Chemistry, vol. 46, 1981, pp. 4433-4438.
Gavalda, et al N-Sulfonyl hydroxamate derivatatives as inhibitors of class II fructose-1, 6-diphosphate aldolase, Bioorganic & Medicinal Chemistry Letter, 2005, vol. 15, No. 24, pp. 5375-5377.
Goldschmidt,St. et al., "Biphenyl derivatives II. Basic 4-Biphenyl Compounds". Receuil Travaux Chimiques Des Pays-Bas, vol. 69, 1950, pp. 1109-1117.
Grothe, V. W. et al. "Effect of Potassium Sulfhydrate etc. on Chloroacetylanilides". Archiv der Pharmazie (Weinheim), vol. 238, 1980, p. 600-614.
Hadjipavlou-Litina, D. et al., "Thiazolyl-N-Substituted Amides: A group of effective anti-inflammatory agents with potential for local anesthetic properties. Synthesis, Biological Evaluation, and a QSAR Approval." Drug Development Research, Vo. 48, 1999, p.53-60.
Hanus, L. et al., "HU-308: A specific agonist for CB2, a peripheral cannabinoid receptor", PNAS, 1999, vol. 96, No. 25, p. 14228.
Herndon, J. L. et al., "Ketanserin analogues. Structure-affinity relationships for 5-HT2 and 5-HT1c serotoninin receptor binding". J. Med. Chem, 1992, vol. 35, No. 26, pp. 4903-4910.
Huang, X. et al., "A Novel Synthesis of Sulfones via the O.O-Diethylphosphorotellurite Ion-assisted Coupling of Arenesulfonyl Chlorides with Active Halides". Synthetic Communications, 20(15), 2291-2291-2295 (1990).
Ibrahim, M. M. et al., "Activation of CB2 cannabinoid receptors by AM1241 inhibits experimental neuropathic pain: Pain inhibition by receptors not present in the CNS", PNAS, 2003, vol. 100, No. 18, p. 10529.
Iddon, B. et al., "Condensed thiophen ring systems. Part SVII. A new synthesis of 10H-indeno[1,2-b][1] benzothiophen". Journal of the Chemical Society. Perkin Transactions 1, Chemical Socieity. Letchworth, GB. vol. 21, Jan. 1, 1974, pp. 2505-2508. ISSN: 0300-922X, p. 2506; compound 8.
Iddon, B. et al., "Polyhalogenoaromatic Compounds. Part 42. C N.m.r. Spectra of Polyhalogeno-pyridines and- pyrimidines". XP009094360, Ramage Laboratories, Dept of Chemistry and Applied Chemistry, University of Salford, Salford M5 4WT, Journal of the Chemical Society, Perkin Transactions 1, 1980, p. 1370.

(56) References Cited

OTHER PUBLICATIONS

Igarashi, J. et al., "Improved synthesis of quinine alkaloids with the Teoc protective group". Tetrahedron letters, Elsevier, Amsterdam, vol. 46, No. 37, 2005, pp. 6381-6384.
Ishii, K. et al., "Smiles Rearrangement of 2-(1-Methyl-1H-tetrazol-5-ylthio)acetamides and their Sulfonyl Derivatives". XP009094359, Chem. Pharm. Bull. 39(12) 3331-3334 (1991).
Johansen et al., AMPA Receptor Agonists: Resolution, Configurational Assignment, and Pharmacology of (+)-(S)- and (-)-(R)-2-Amino-3-(3-Hydroxy-5-(2-Pyridyl) Isoxazol-4-yl)Propionic Acid (1-Py-AMPA); Chirality, New York, 1997, vol. 9, No. 3, pp. 274-280.
Kano, S. et al., "Formation of Some Heterocycles through Ring Transformation of 1-Arylaxetidin-2-Ones." Heterocycles, vol. 8, No. 1, Dec. 30, 1977, p. 411-416.
Katoh, A., et al., "Synthesis of 6-(Bromoacetyl)Amino-2,3-Dimorpholino-Quinoxaline and Application to a new Fluorescence Derivatization Reagent of Fatty Acids for the High-Performance Liquid Chromatographic Analysis", Heterocycles, 1999, vol. 50, No. 1, p. 299.
Katz, L., et al., "Hydrazine Derivatives. II. Ortho-Mercapto-Pyridinecarbohydrazides", Contribution from Schenley Laboratories, Inc., 1953, p. 711.
Klein, T. W., et al., "The Cannabinoid system and immune modulation", J. Leukocyte Biology, 2003, vol. 74, p. 486.
Kolehmainen, E. et al., "a-Phenylsulfonyl-N-arylacetamides (a-phenylsulfonylacetanilides): H, C and N NMR spectral characterization". XP002465784, Magnetic Resonance in Chemistry, 2000, 38: 384-385.
Krutosikova, A. et al., "Furan derivatives. LV. Preparation of 5-aryl-2-furfuryl phenyl and 5-aryl-2-furfuryl 4-tolyl sulfones". Chemick Zvesti—Chemical Papers, Veda Bratislava, SK. vol. 28, Jan. 1, 1974, pp. 414-417, ISSN: 0366-6352, p. 414, compounds I-IX.
Lambeng, N. et al., "Discovery of a Novel Piperidinyl-Sulfonyl Benzoic Ester, Active as CB1 Agonist" POSTER. 231st ACS National Meeting, Atlanta, GA. Mar. 26-30, 2006.
Lesser, R. et al. "Homo-?-oxythionaphthene (4-Ketoisothiochromane". Charlottenburg, Industrial Chemistry Laboratory of the Institute of Technology, 1923, pp. 1642-1648.
Lutz, R. E. et al., "Antimalarials. Some piperazine derivatives". Journal of Organic Chemistry, vol. 12, 1947, pp. 771-775.
Mahmoud, A. M. et al., "Synthesis and Biological Activity of Some new 2-(N-Substituted Carboxamidomethyl Thio)-Naphth[1,2-d]Oxazoles—Part V". XP002068972, J. Indian Chem. Soc., vol. LIX, May 1982, pp. 675-677.
Malan Jr., T. P., et al., "CB2 cannabinoid receptor-mediated peripheral antinociception", PAIN, 2001, vol. 93, p. 239.
Markley, L. D., et al., "Antipicornavirus activity of substituted Phenoxybenzenes and Phenoxypyridines", J. Med. Chem., 1986, vol. 29, p. 427.
Marx, I. E. et al., "Discovery of a-amidosulfones as potent and selective agonists of CB2: Synthesis, SAR, and pharmacokinetic properties". Bioorganic and Medicinal Chemistry Letters, 2009, p. 31-35. In press, accepted manuscript.
Messinger, P., "Sulfones via Mannich bases" Archiv der Pharmazie, 1973, vol. 306, No. 8, pp. 603-610, ISSN: 0365-6233. p. 607, compounds 28A-29C.
Miroshnikova, O.V. et al., "Structure-activity relationships in the series of eremomycin carboxamides". Journal of Antibiotics, vol. 53, No. 3, 2000, pp. 286-293.
Miyano, S, et al., "Kinetic Resolution of Racemic b-Hydroxy Amines by Enantioselective N-Oxide formation". Journal of Organic Chemistry, 1985, vol. 50, pp. 4350-4360.
Mohler, et al., "Nonsteroidal tissue selective androgen receptor modulators: a promising class of clinical candidates" University of Tennessee Health Science Center, Expert Opinion of Therapeutic Patents; Nov. 2005, vol. 15, No. 11, pp. 1565-1585.
Nackley, A. G., et al., "Selective Activation of Cannabinoid CB2 Receptors Suppresses Spinal FOS Protein Expression and Pain Behavior in a rat Model of Inflammation", Neuroscience, vol. 119, 2003, p. 747.

Office Action from the EPO for 09-0388 dated Mar. 22, 2010.
Office Action mailed Jan. 13, 2012 for U.S. Appl. No. 12/882,328, filed Sep. 15, 2010. Inventor: Alessandra Bartolozzi.
Office Action mailed Jan. 27, 2012 for U.S. Appl. No. 12/741,260, filed Jun. 17, 2010. Inventor: Angela Berry.
Pollard, C. B. et al., "Some amides of piperazines". Journal of American Chemical Society, vol. 75, 1953, p. 491.
Revesz, L. et al., "Novel CCR1 antagonists with oral activity in the mouse collagen induced arthritis". Bioorganic and Medicinal Chemistry Letters, vol. 15, 2005, pp. 5160-5164.
Sakuraba, S, et al., "Efficient asymmetric hydrogenation of a-amino ketone derivatives. A highly enantioselective synthesis of phenylephrine, levamisole, carnitine and propranolol". Chemical and Pharmaceutical Bulletin, Pharm. Society of Japan, 1995, vol. 43, No. 5, pp. 738-747.
Schaefer, H. et al. "On the Synthesis of 4-aminoquinolines and -quinolinones-(2) from Anthranilonitrile" Chemistry Department of the Technical University of Dresden, Journal for Practical Chemistry, vol. 321, No. 4, 1979, pp. 695-698.
Seidel M. C. et al., "Heterocyclic Rearrangements. XII. The Formation of a Formylbenzofurazan oxide from a nitroanthranil". Journal of Organic Chemistry, vol. 35, No. 5, May 1970, p. 1662-1664.
Sharkey, K. A. et al., "CB2 cannabinoid receptors: new vistas", The first International Conference devoted to studies of the CB2 cannabinoid receptor. Banff, Alberta, Canada, May 31-Jun. 3, 2007.
Sheehan, J.C. et al, The Synthesis and Reactions of Some Substitued Beta-Lactams, 1951, Journal of the American Chemical Society, 73, 1761-1765.
Sisko, J. et al., "An investigation of imidazole and oxazole synthesis using aryl-substituted TosMIC reagents". The Journal of Organic Chemistry, vol. 65, No. 5, Mar. 10, 2000, pp. 1516-1624, ISSN: 022-3263, p. 1523, table 5, compound 69.
Smith, S. R., et al., "The anti-inflammatory activities of cannabinoid receptor ligands in mouse peritonitis models", Eur. J. Pharmacology, 2001, vol. 432, p. 107.
Strating, J., et al. "Nucleophilic Additions to Bis-Tertiobutyl Sulfonyl Acetylene (Properties of the sulfonyl group XLIV 1)". University of Groningue, Organic Chemistry Laboratory, 1954, pp. 709-716.
Swanson, D. M. et al., "Identification and biological evaluation of 4-*(3-trifluoromethylpyridin-2-yl)piperzine-1-carboxylic acid (5-trifluoremethylpyridin-2-yl)amide, a high affinity TRPV1 (VR1) vanilloid receptor antagonist". Journal Med. Chem, 2005, 48, pp. 1857-1872.
Tegley, et al., "Discovery of Novel Hydroxy-Thiazoles as HIF-alpha Prolyl Hydroxylase Inhibitors: SAR, Synthesis, and Modeling Evaluation," Bioorganic & Medicinal Chemistry Letters, Pergamon, Elsevier Science, GB, vol. 18, No. 14, 2008, pp. 3925-3928.
Todorova, T. R., et al "Ring-enlargement and ring-opening reactions of 1,2-thiazetidin-3-one 1,1,-dioxides with ammonia and primary amines as nucleophiles". Helvetica Chimica Acta, vol. 82, 1999, pp. 354.
Troeger, J. et al., "Regarding sulfonated Butyric Acids". From the Laboratory for Pharmaceutical and Synthetic Chemistry of the Braunschweig Institute of Technology.1991, 40, 506.
Troeger, J. and Uhde, R., "Ueber sulfonirte buttersauren", J. Prakt. Chem., 1899, 1991, vol. 59, p. 320.
Tweit, R. C., et al., "Synthesis of Antimicrobial Nitroimidazolyl 2-Sulfides, -Sulfoxides, and -Sulfones". Dept. of Chemical and Biological Research, Searle Laboratories, Chicago, IL, USA, Mar. 29, 1973, pp. 1161-1169.
U.S. Appl. No. 13/022,866, filed Feb. 8, 2011, Inventor: Angela Berry.
U.S. Appl. No. 13/037,422, filed Mar. 1, 2011, Inventor: Monika Ermann.
Ueda, Y., et al., "Involvement of cannabinoid CB2 receptor-mediated response and efficacy of cannabinoid CB2 receptor inverse agonist, JTE-907, in cutaneous inflammation in mice", Eur. J. Pharmacology, 2005, vol. 520, p. 164.
Van Sickle, M. D., et al., "Identification and Functional Characterization of Brainstem Cannabinoid CB2 receptors", Science, 2005, vol. 310, p. 329.

(56) References Cited

OTHER PUBLICATIONS

Venkov, A.P. et al., "A new synthesis of 1,2,3,4tetrahydro-2-methyl-4-phenylisoquinolines". Dept of Chemistry, University of Plovdiv, Bulgaria, pp. 253-255, Mar. 1990.

Vogtle, M. M. et al., "An efficient protocol for the solid-phase synthesis of malondiamides". Molecules, 2005, 10, pp. 1438-1445. XP002481324.

Walker, G.N. et al., "Synthesis of varied heterocyclic and substituted aryl alkyl secondary amines, related Schiff bases, and amides". Journal of Medicinal Chemistry, vol. 9, 1966, pp. 624-630.

Wang, Y. et al., "Rapid and efficient synthesis of 1,2,4-oxadiazoles utilizing polymer-supported reagents under microwave heating". Organic Letters, vol. 7, No. 5, Mar. 3, 2005, pp. 925-928, ISSN: 1523-7060, p. 927, compounds 14,15.

Watson, R. J., et al "An enantioselective synthesis of sulphonamide hydroxamic acids as matrix metalloproteinase inhibitors", Pergamon, Tetrahedron Letters 43 (2002) 683-685.

Yang, G. et al., "Synthesis and Bioactivity of Novel Triazolo [1,5-a]Pyrimidine Derivatives[3]". XP002465786, Heteroatom Chemisry, vol. 12, No. 6, 2001, p. 491-496.

Yokoyama, M. et al., "A regioselective synthesis of 3 5 disubstituted isoxazoles". Journal of the Chemical Society Perkin Transactions I, No. 1, 1986, pp. 67-72, ISSN: 0300-922X, pp. 68,69, compounds 6A, 14A.

Yordanova, K. et al. "New method for the synthesis of 2,4-disubstituted morpho-lines". Chemical Abstracts, vol. 97, No. 17, Oct. 25, 1982, Columbus, Ohio, USA Chemical Abstracts, vol. 97, No. 17, Oct. 25, 1982, Columbus, Ohio, vol. 115, No. 7, pp. 2635-2642.

Zhang, B. and Breslow, R., "Ester Hydrolysis by a Catalytic Cyclodextrin Dimer Enzyme Mimic with a Metallobipyridyl Linking Group", J. Am. Chem. Soc., 1997, vol. 119, p. 1676.

Zimmer, A. et al., "Increased mortality, Hypoactivity, and hypoalgesia in cannabinoid CB1 receptor knockout mice", Proc. Natl. Acad. Sci. USA, 1999, vol. 96, p. 5780.

Zindell, R. et al., "Discovery of a novel class of CB2 agonists". General Poster Session. The 235th ACS National Meeting, New Orleans, LA, USA. Apr. 6-10, 2008.

\* cited by examiner

COMPOUNDS WHICH MODULATE THE CB2 RECEPTOR

APPLICATION DATA

This application claims priority to U.S. provisional application Ser. No. 61/295,201 filed Jan. 15, 2010.

BACKGROUND OF THE INVENTION

1. Technical Field

The present invention relates to novel compounds which modulate the CB2 receptor and their use as medicaments.

2. Background Information

Cannabinoids are a group of about 60 distinct compounds found in *Cannabis sativa* (also know as marijuana) with cannabinol, cannabidiol and $\Delta^9$-tetrahydrocannabinol (THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on THC and its analogous nabilone, respectively, are used as anti-emetic and appetite stimulant. Despite of the clinical benefits, the therapeutic usage of cannabis is limited by its psychoactive effects including hallucination, addiction and dependence. Mechoulam R, ed. *Cannabinoids as Therapeutic Agents*, Boca Raton, Fla.; CRC Press, 1986 provides a review of the medicinal use of cannabis.

The physiological effects of cannabinoids are mediated by at least two G-protein coupled receptors, CB1 and CB2. Autoradiographic studies have demonstrated that CB1 receptors are expressed primarily in the central nervous system, specifically in the cerebral cortex, hippocampus, basal ganglia and cerebellum. They are also found to a lesser degree in the reproductive system and other peripheral tissues including that of the immune system. CB1 receptors regulate the release of neurotransmitters from the pre-synaptic neurons and are believed to mediate most of the euphoric and other central nervous system effects of cannabis, such as THC-induced ring-catalepsy, hypomobility, and hypothermia, which were found to be completely absent in mice with a deletion of the CB1 gene (Zimmer et al., Increased mortality, hypoactivity, and hypoalgesia in cannabinoid CB1 receptor knockout mice. Proc Natl Acad Sci USA. (1999) 96:5780-5785.)

CB2 receptors are almost exclusively found in the immune system, with the greatest density in the spleen. It is estimated that the expression level of CB2 in the immune cells is about 10 to 100 times higher than CB1. Within the immune system, CB2 is found in various cell types, including B cells, NK cells, monocytes, microglial cells, neutrophils, T cells, dentritic cells and mast cells, suggesting that a wide range of immune functions can be regulated through CB2 modulators (Klein et al., The cannabinoid system and immune system. J Leukoc Biol (2003) 74:.486-496). This is supported by the finding that the immunomodulatory effect of THC is absent in CB2 deficient mice mice (Bicklet et al., Immunomodulation by cannabinoid is absent in mice deficient for the cannabinoid CB2 receptor. Eur J Pharmacol (2000) 396:141-149). CB2 selective ligands have been developed and tested for their effects in various inflammatory settings. For example, in animal models of inflammation, CB2 selective agonists, inverse agonists and antagonists have been shown to be effective in suppressing inflammation (Hanus et al., HU-308: a specific agonist for CB(2), a peripheral cannabinoid receptor. Proc Natl Acad Sci USA. (1999) 96:14228-14233, Ueda et al., Involvement of cannabinoid CB(2) receptor-mediated response and efficacy of cannabinoid CB(2) receptor inverse agonist, JTE-907, in cutaneous inflammation in mice. Eur J Pharmacol. (2005) 520:164-171 and Smith et al., The anti-inflammatory activities of cannabinoid receptor ligands in mouse peritonitis models Eur J Pharmacol. (2001) 432:107-119.). Furthermore, CB2 selective agonists inhibit disease severity and spasticity in animal models for multiple sclerosis (Baker et al., Cannabinoids control spasticity and tremor in a multiple sclerosis model. Nature (2000) 404:84-87. Arevalo-Martin et al., Therapeutic action of cannabinoids in a murine model of multiple sclerosis J Neurosci. (2003) 23:2511-2516.). Taken together, these results support the notion that CB2 receptor modulators can be employed for the treatment of medical conditions having an inflammatory component.

In addition to inflammation, CB2 agonists have been shown to inhibit pain and emesis. For instance, CB2 selective agonists blunt the pain response induced by thermal or other stimuli (Malan et al., CB2 cannabinoid receptor-mediated peripheral antinociception. Pain. (2001) 93:239-45 and Nackley et al., Selective activation of cannabinoid CB(2) receptors suppresses spinal fos protein expression and pain behavior in a rat model of inflammation. Neuroscience (2003) 119:747-57.) CB2 activation has also been demonstrated to inhibit neuropathic pain response (Ibrahim et al., Activation of CB2 cannabinoid receptors by AM1241 inhibits experimental neuropathic pain: pain inhibition by receptors not present in the CNS. Proc Natl Acad Sci USA. (2003) 100: 10529-33.) Finally, in contrast to the earlier data which did not find CB2 in the brain, a recent article demonstrated the expression of CB2 in the brain, at about 1.5% of the level in the spleen. CB2 activation is shown by this article to be responsible for the anti-emetic effect of endocannabinoid (Van Sickle et al., Identification and functional characterization of brainstem cannabinoid CB2 receptors. Science. 2005 310:329-332.) The foregoing results confirm that CB2 agonists can be used for the treatment of inflammatory and neuropathic pain as well as emesis.

WO2008014199 and WO2008039645 discuss the CB2 receptor and the therapeutic uses of the sulfone derivatives, having CB2 agonist activity, disclosed therein.

BRIEF SUMMARY OF THE INVENTION

The present invention provides novel compounds which bind to and modulate the CB2 receptor. The invention also provides methods and pharmaceutical compositions for treating inflammation by way of the administration of therapeutic amounts of the compounds of the invention. Lastly, the invention provides a method and pharmaceutical compositions for treating pain by way of the administration of therapeutic amounts of the compounds of the invention.

DETAILED DESCRIPTION OF THE INVENTION

In the broadest generic embodiment 1, the invention provides compounds of the formula

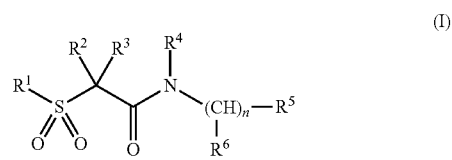

(I)

wherein:

$R^1$ is $C_{1-10}$ alkyl, $C_{3-10}$ cycloalkyl, 3-10 membered saturated heterocyclic ring, $C_{1-5}$ alkyl-heterocyclic ring, 5-10 membered mono or bicyclic aryl ring or $C_{1-5}$ alkyl-aryl ring, wherein each $R^1$ is optionally independently substituted with 1-3 substituents chosen from $C_{1-4}$ alkyl group optionally substituted with 1-3 halogens, $C_{3-10}$ cycloalkyl, $C_{1-4}$ alkoxy, $C_{1-4}$ alkylsulfonyl, acyl, cyano, hydroxyl and halogen;

$R^2$ and $R^3$ are $C_{1-4}$ alkyl or hydrogen with the proviso that both $R^2$ and $R^3$ cannot be hydrogen; or $R^2$ and $R^3$ together with the carbon atom to which they are attached form a 3- to 6-membered cycloalkyl ring;

$R^4$ is hydrogen or methyl;

$R^5$ is $C_{1-10}$ alkyl, $C_{3-10}$ cycloalkyl, 3-10 membered saturated heterocyclic ring, 5-10 membered mono or bicyclic aryl ring, 5-10 membered mono or bicyclic heteroaryl ring, —S—$C_{1-5}$ alkyl, —S-aryl, —S—$CH_2$-aryl, —O—$C_{1-5}$ alkyl, —O-aryl, —O—$CH_2$-aryl, —NH—$C_{1-5}$ alkyl, —NH-aryl, —NH—$CH_2$-aryl or amino wherein each $R^5$ is optionally independently substituted with 1-3 substituents chosen from $C_{1-4}$ alkyl group optionally substituted with 1-3 halogens, $C_{1-4}$ alkoxy, acyl, —C(O)-heteroaryl, cyano, hydroxyl and halogen;

when n=0, $R^4$ and $R^5$ together with the nitrogen atom to which they are attached, optionally form a 4-7 membered heterocyclic ring which is optionally substituted with a substituent chosen from aryl, —C(O)—O—$C_{1-5}$ alkyl, —C(O)— heteroaryl, —C(O)-aryl, —$SO_2$-heteroaryl and —$SO_2$-aryl;

$R^6$ is hydrogen or $C_{1-4}$ alkyl;

n is 0, 1, 2, 3 or 4;

wherein any carbon atom on the formula (I) or any R substituent listed above is optionally partially or fully halogenated where possible;

or a pharmaceutically acceptable salt thereof.

In another embodiment 2, the invention provides compounds of the formula (I) according to the preceding generic embodiment described above, and wherein $R^1$ is $C_{1-6}$ alkyl, phenyl, cyclopropyl, cyclobutyl, cyclopentyl, cyclohexyl, cycloheptyl, cyclooctyl, —$CH_2$-cyclopropyl, —$CH_2$-cyclobutyl, tetrahydrofuranyl, tetrahydropyranyl, azetidinyl, piperidinyl; thiomorpholinyl, 1,1-Dioxo-1$\lambda^6$-thiomorpholinyl, morpholinyl, pyrrolidinyl, piperazinyl, benzyl, —$CH_2$-tetrahydrofuranyl, —$CH_2$-tetrahydropyranyl, —$CH_2$—$CH_2$-tetrahydrofuranyl or —$CH_2$—$CH_2$-tetrahydropyranyl wherein each $R^1$ is optionally independently substituted with 1-3 substituents chosen from $C_{1-4}$ alkyl group optionally substituted with 1-3 halogens, $C_{1-4}$ alkoxy, $C_{1-4}$ alkylsulfonyl, acyl, cyano, hydroxyl and halogen;

$R^2$ and $R^3$ are independently methyl, ethyl, n-propyl, iso-propyl, t-Bu, or hydrogen with the proviso that both $R^2$ and $R^3$ cannot be hydrogen; or $R^2$ and $R^3$ together with the carbon to which they are attached form a cyclopropyl, cyclobutyl, or cyclopentyl ring;

$R^4$ is hydrogen or methyl;

$R^5$ is $C_{is}$ alkyl, phenyl, cyclopropyl, cyclobutyl, cyclopentyl, cyclohexyl, cycloheptyl, cyclooctyl, tetrahydrofuranyl, tetrahydropyranyl, azetidinyl, piperidinyl; thiomorpholinyl, 1,1-Dioxo-1$\lambda^6$-thiomorpholinyl, morpholinyl, pyrrolidinyl, piperazinyl, indanyl, benzoxazolyl, benzothiazolyl, benzimidazolyl, oxazolyl, isoxazolyl, thiazolyl, pyrazolyl, pyrrolyl, imidazolyl, thienyl, thiadiazolyl, pyridinyl, pyrimidinyl, pyridazinyl, pyrazinyl, triazinyl, quinolinyl, Dihydro-2H-quinolinyl, isoquinolinyl, quinazolinyl, indazolyl, indolyl, benzofuranyl, benzopyranyl, benzodioxolyl, —S—$C_{1-5}$ alkyl, —S-phenyl, —S—$CH_2$-phenyl, —O—$C_{1-5}$ alkyl, —O-phenyl, —O—$CH_2$-phenyl, —NH—$C_{1-5}$ alkyl, —NH-phenyl, —NH—$CH_2$-phenyl or amino wherein each $R^5$ is optionally independently substituted with 1-3 substituents chosen from $C_{1-4}$ alkyl group optionally substituted with 1-3 halogens, $C_{1-4}$ alkoxy, acyl, —C(O)-heteroaryl, cyano, hydroxyl and halogen;

when n=0, $R^4$ and $R^5$ together with the nitrogen atom to which they are attached, optionally form a 4-7 membered heterocyclic ring containing 0 or 1 additional heteroatom and which is optionally substituted with a substituent chosen from phenyl, —C(O)—O—$C_{1-5}$ alkyl, —C(O)-thienyl, —C(O)-phenyl, —$SO_2$-heteroaryl and —$SO_2$-phenyl;

$R^6$ is hydrogen or $C_{1-3}$ alkyl;

In another embodiment 3, the invention provides compounds of the formula (I) according to any of the preceding embodiments, and wherein $R^1$ is $C_{1-6}$ alkyl, phenyl, cyclopentyl, cyclohexyl, tetrahydropyranyl, benzyl or —$CH_2$-tetrahydropyranyl wherein each $R^1$ is optionally independently substituted with 1-3 substituents chosen from $C_{1-4}$ alkyl group optionally substituted with 1-3 halogens, $C_{1-4}$ alkoxy, $C_{1-4}$ alkylsulfonyl, and halogen;

In another embodiment 4, the invention provides compounds of the formula (I) according to any of the preceding embodiments, and wherein $R^2$ and $R^3$ are independently methyl, or $R^2$ and $R^3$ together with the carbon to which they are attached form a cyclobutyl ring;

In another embodiment 5, the invention provides compounds of the formula (I) according to any of the preceding embodiments described above, and wherein $R^4$ is hydrogen or methyl;

$R^5$ is $C_{1-5}$ alkyl, phenyl, cyclohexyl, cycloheptyl, morpholinyl, indanyl, isoxazolyl, thienyl, pyridinyl, —S—$C_{1-5}$ alkyl, —S-phenyl, —S—$CH_2$-phenyl, —O—$C_{1-5}$ alkyl, —O-phenyl, —NH—$C_{1-5}$ alkyl, —NH-phenyl or amino wherein each $R^5$ is optionally independently substituted with 1-3 substituents chosen from $C_{1-4}$ alkyl group optionally substituted with 1-3 halogens, $C_{1-4}$ alkoxy, acyl, and halogen;

In a another embodiment 6, the invention provides compounds of the formula (I) according to any of the preceding embodiments 1-4, and wherein when n=0, $R^4$ and $R^5$ together with the nitrogen atom to which they are attached optionally form a 4-7 membered heterocyclic ring containing 0 or 1 additional heteroatom and which is optionally substituted with a substituent chosen from phenyl, —C(O)—O—$C_{1-4}$ alkyl, —C(O)-thienyl and —$SO_2$-phenyl;

In a another embodiment 7, the invention provides compounds of the formula (I) according to embodiment 2, and wherein $R^1$ is $C_{1-6}$ alkyl, phenyl, cyclopentyl, cyclohexyl, tetrahydropyranyl, benzyl or —$CH_2$-tetrahydropyranyl wherein each $R^1$ is optionally independently substituted with 1-3 substituents chosen from $C_{1-4}$ alkyl group optionally substituted with 1-3 halogens, $C_{1-4}$ alkoxy, $C_{1-4}$ alkylsulfonyl, and halogen;

$R^2$ and $R^3$ are independently methyl, or $R^2$ and $R^3$ together with the carbon to which they are attached form a cyclobutyl ring;

$R^4$ is hydrogen or methyl;

$R^5$ is $C_{1-5}$ alkyl, phenyl, cyclohexyl, cycloheptyl, morpholinyl, indanyl, isoxazolyl, thienyl, pyridinyl, —S—$C_{1-5}$ alkyl, —S-phenyl, —S—$CH_2$-phenyl, —O—$C_{1-5}$ alkyl, —O-phenyl, —NH—$C_{1-5}$ alkyl, —NH-phenyl or amino wherein each $R^5$ is optionally independently substituted with 1-3 substituents chosen from $C_{1-4}$ alkyl group optionally substituted with 1-3 halogens, $C_{1-4}$ alkoxy, acyl, and halogen;

when n=0, R⁴ and R⁵ together with the nitrogen atom to which they are attached, optionally form piperidinyl or piperazinyl which is optionally substituted with a substituent chosen from phenyl, —C(O)—O—C₁₋₄ alkyl, —C(O)—thienyl and —SO₂-phenyl;

R⁶ is hydrogen or methyl;

n is 0, 1, 2 or 3

In another embodiment 8, the invention provides compounds of the formula (I) according embodiment 7 above and wherein R¹ is phenyl, cyclohexyl or benzyl wherein each R¹ is optionally independently substituted with 1-2 substituents chosen from trifluoromethyl, and chloro;

R² and R³ are methyl, or

R² and R³ together with the carbon to which they are attached form a cyclobutyl ring;

R⁴ is hydrogen;

R⁵ is C₁₋₄ alkyl, phenyl, cyclohexyl, cycloheptyl, thienyl, —S—C₁₋₅ alkyl, —S-phenyl, —S—CH₂-phenyl, —O—C₁₋₅ alkyl, —O-phenyl or —NH-phenyl wherein each R⁵ is optionally independently substituted with 1-3 substituents chosen from C₁₋₄ alkyl, trifluoromethyl, C₁₋₄ alkoxy, fluoro and chloro;

In another embodiment 9, the invention provides compounds of the formula (I) according to embodiment 7, and wherein when n=0, R⁴ and R⁵ together with the nitrogen atom to which they are attached, optionally form piperidinyl or piperazinyl which is optionally substituted with a substituent chosen from phenyl, —C(O)—O—C₁₋₄ alkyl and —C(O)—thienyl;

In another embodiment 10, the invention provides compounds of the formula (I) according to embodiment 8, and wherein R¹ is phenyl or cyclohexyl each optionally substituted by a substituent chosen from trifluoromethyl, and chloro;

R² and R³ are methyl, or

R² and R³ together with the carbon to which they are attached form a cyclobutyl ring;

R⁴ is hydrogen;

R⁵ is C₁₋₄ alkyl, phenyl, cyclohexyl, —S—C₁₋₅ alkyl, —S-phenyl or —S—CH₂-phenyl, wherein each R⁵ is optionally independently substituted with 1-3 substituents chosen from C₁₋₄ alkyl, trifluoromethyl, methoxy, fluoro and chloro;

n is 0 or 2.

In another embodiment 11, the invention provides compounds of the formula (I) according to embodiment 9, and wherein when n=0, R⁴ and R⁵ together with the nitrogen atom to which they are attached form a piperazinyl ring which is substituted with a phenyl group;

In another embodiment 12 the invention provides compounds of the formula (I) according to any of the preceding embodiments described above, and wherein R² and R³ are methyl;

In another embodiment 13 the invention provides compounds of the formula (I) according to any of the preceding embodiments 1-12, and wherein R² and R³ together with the carbon to which they are attached form a cyclobutyl ring.

In another embodiment there is provided a compound of the formula (IA)

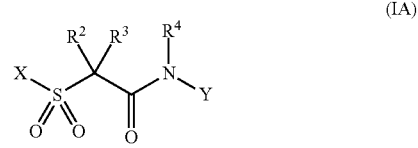

(IA)

wherein

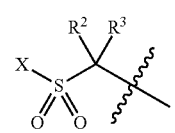

of the formula (IA) is chosen from column A1-A16 in Table I, and

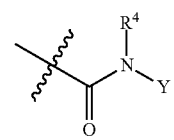

of the formula (IA) is chosen from column B1-B48 in Table I,

TABLE I

| A1 | ₂-) |
|----|-----|
| A2 | ₂-) |
| A3 | ₂-) |
| A4 | |

TABLE I-continued
| | | | | |
|---|---|---|---|---|
| A5 | 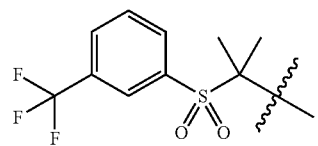 [SMILES: *C(C)(C)S(=O)(=O)c1cccc(C(F)(F)F)c1] | | A15 | 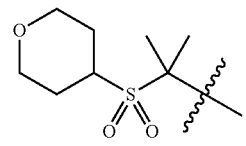 |
| A6 | 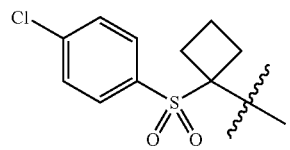 [SMILES: *C1(S(=O)(=O)c2ccc(Cl)cc2)CCC1] | | A16 | 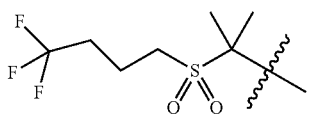 |
| A7 | 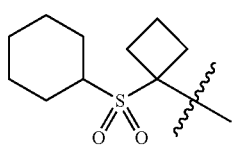 [SMILES: *C1(S(=O)(=O)C2CCCCC2)CCC1] | | B1 | 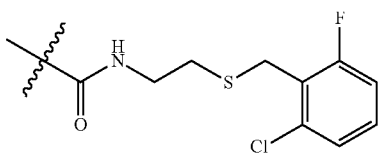 |
| A8 | 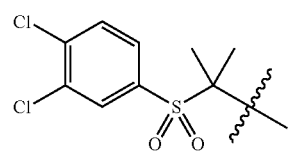 [SMILES: *C(C)(C)S(=O)(=O)c1ccc(Cl)c(Cl)c1] | | B2 | 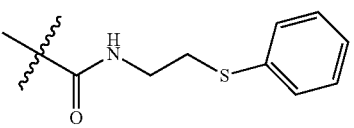 |
| A9 | 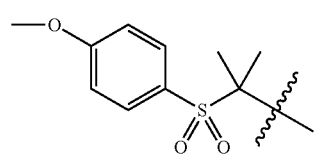 [SMILES: *C(C)(C)S(=O)(=O)c1ccc(OC)cc1] | | B3 | 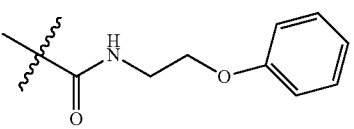 |
| A10 | 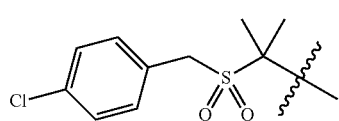 [SMILES: *C(C)(C)S(=O)(=O)Cc1ccc(Cl)cc1] | | B4 | 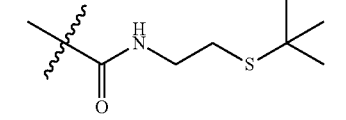 |
| A11 | 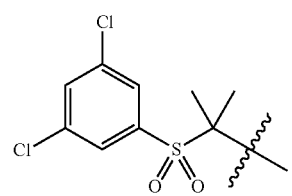 [SMILES: *C(C)(C)S(=O)(=O)c1cc(Cl)cc(Cl)c1] | | B5 | 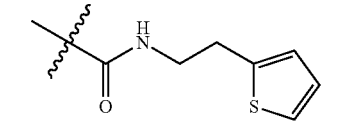 |
| A12 | 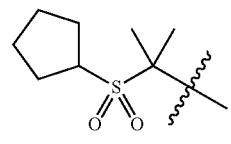 [SMILES: *C(C)(C)S(=O)(=O)C1CCCC1] | | B6 | 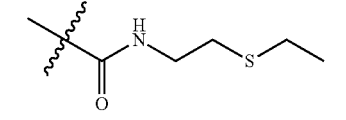 |
| A13 | 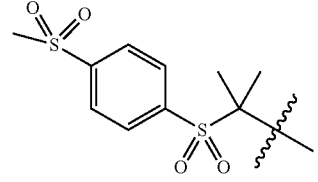 [SMILES: *C(C)(C)S(=O)(=O)c1ccc(S(C)(=O)=O)cc1] | | B7 | 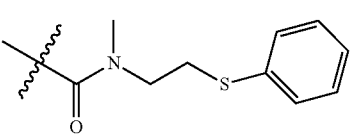 |
| | | | B8 | 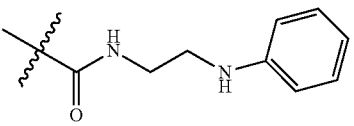 |
| A14 | 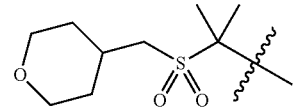 [SMILES: *C(C)(C)S(=O)(=O)CC1CCOCC1] | | B9 | 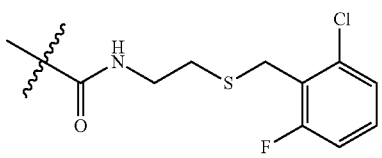 [SMILES: *C(=O)NCCSCc1c(F)cccc1Cl] |

TABLE I-continued
| | |
|---|---|
| B10 | 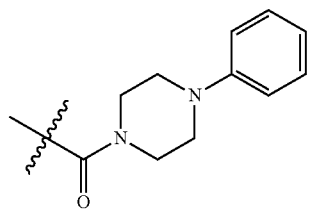 [SMILES: *C(=O)N1CCN(c2ccccc2)CC1] |
| B11 | 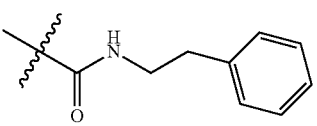 [SMILES: *C(=O)NCCc1ccccc1] |
| B12 | 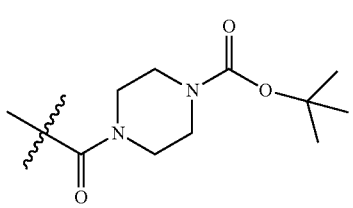 [SMILES: *C(=O)N1CCN(C(=O)OC(C)(C)C)CC1] |
| B13 | 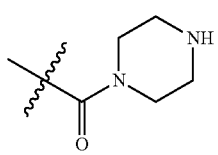 [SMILES: *C(=O)N1CCNCC1] |
| B14 | 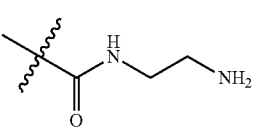 [SMILES: *C(=O)NCCN] |
| B15 | 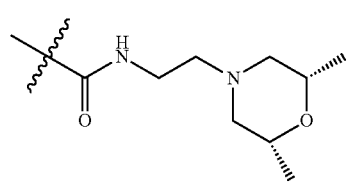 [SMILES: *C(=O)NCCN1C[C@@H](C)O[C@@H](C)C1] |
| B16 | 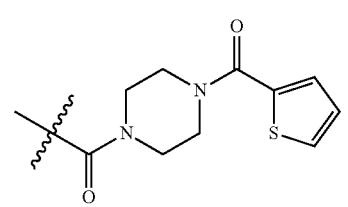 [SMILES: *C(=O)N1CCN(C(=O)c2cccs2)CC1] |
| B17 | 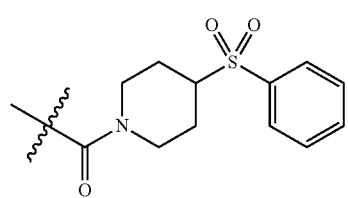 [SMILES: *C(=O)N1CCC(S(=O)(=O)c2ccccc2)CC1] |
| B18 | 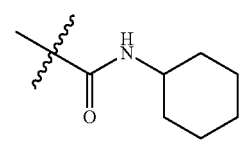 |
| B19 | 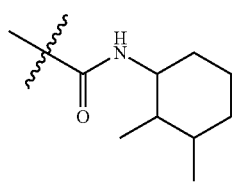 [SMILES: *C(=O)NC1CCCC(C)C1C] |
| B20 | 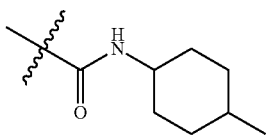 [SMILES: *C(=O)NC1CCC(C)CC1] |
| B21 | 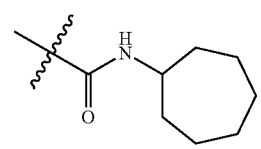 [SMILES: *C(=O)NC1CCCCCC1] |
| B22 | 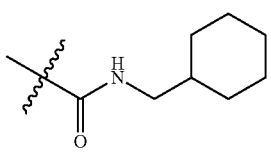 [SMILES: *C(=O)NCC1CCCCC1] |
| B23 | 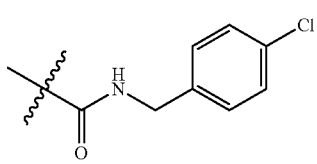 [SMILES: *C(=O)NCc1ccc(Cl)cc1] |
| B24 | 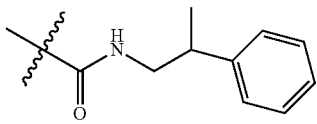 [SMILES: *C(=O)NCC(C)c1ccccc1] |
| B25 | 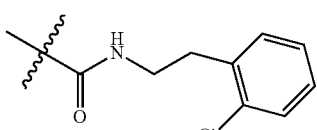 |
| B26 | 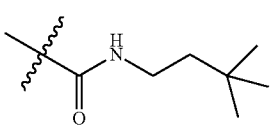 [SMILES: *C(=O)NCCC(C)(C)C] |
| B27 | 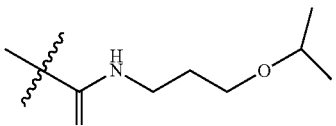 |
| B28 | 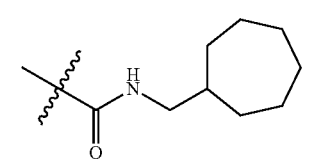 [SMILES: *C(=O)NCC1CCCCCC1] |

TABLE I-continued
B29 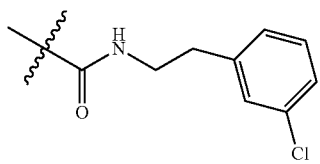 [SMILES: *C(=O)NCCc1cccc(Cl)c1]
B30 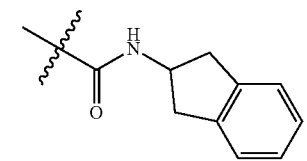 [SMILES: *C(=O)NC1Cc2ccccc2C1]
B31 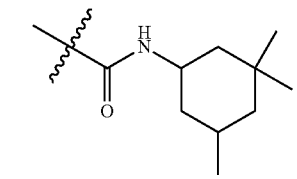 [SMILES: *C(=O)NC1CC(C)CC(C)(C)C1]
B32 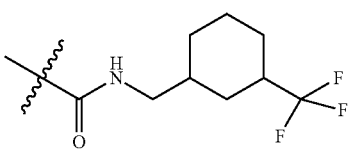 [SMILES: *C(=O)NCC1CCCC(C(F)(F)F)C1]
B33 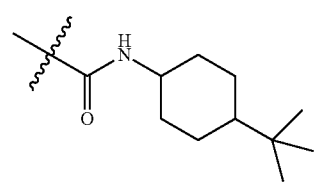 [SMILES: *C(=O)NC1CCC(C(C)(C)C)CC1]
B34 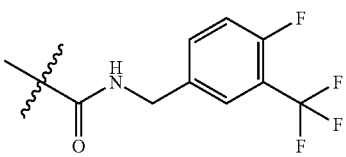 [SMILES: *C(=O)NCc1ccc(F)c(C(F)(F)F)c1]
B35 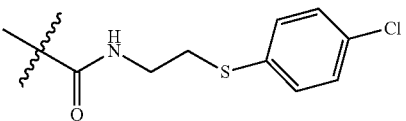 [SMILES: *C(=O)NCCSc1ccc(Cl)cc1]
B36 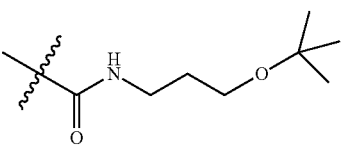 [SMILES: *C(=O)NCCCOC(C)(C)C]
B37 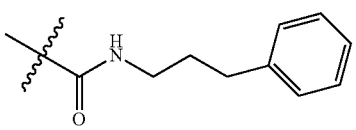
B38 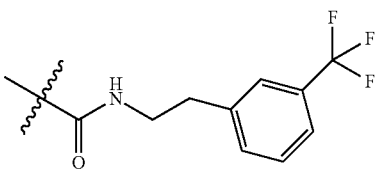 [SMILES: *C(=O)NCCc1cccc(C(F)(F)F)c1]
TABLE I-continued
B39 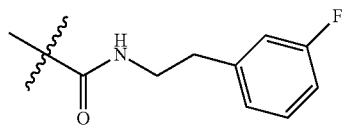 [SMILES: *C(=O)NCCc1cccc(F)c1]
B40 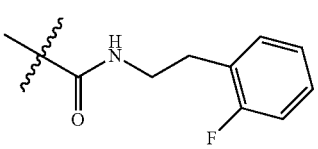 [SMILES: *C(=O)NCCc1ccccc1F]
B41 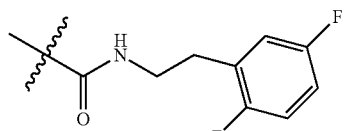
B42 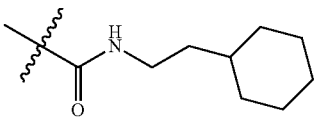 [SMILES: *C(=O)NCCC1CCCCC1]
B43 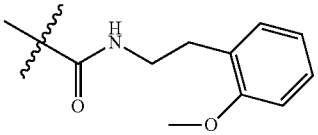 [SMILES: *C(=O)NCCc1ccccc1OC]
B44 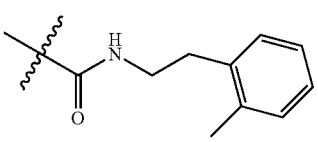 [SMILES: *C(=O)NCCc1ccccc1C]
B45 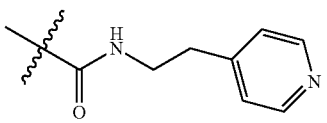 [SMILES: *C(=O)NCCc1ccncc1]
B46 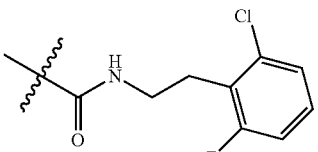
B47 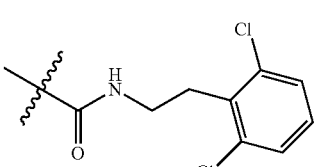
B48 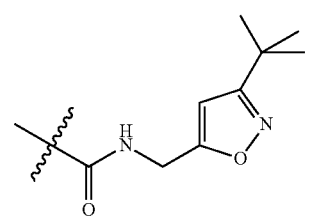 [SMILES: *C(=O)NCc1cc(C(C)(C)C)no1]
or a pharmaceutically acceptable salt thereof.

In another embodiment, the invention provides made compounds in Table II which can be made in view of the general schemes, examples and methods known in the art.
TABLE II
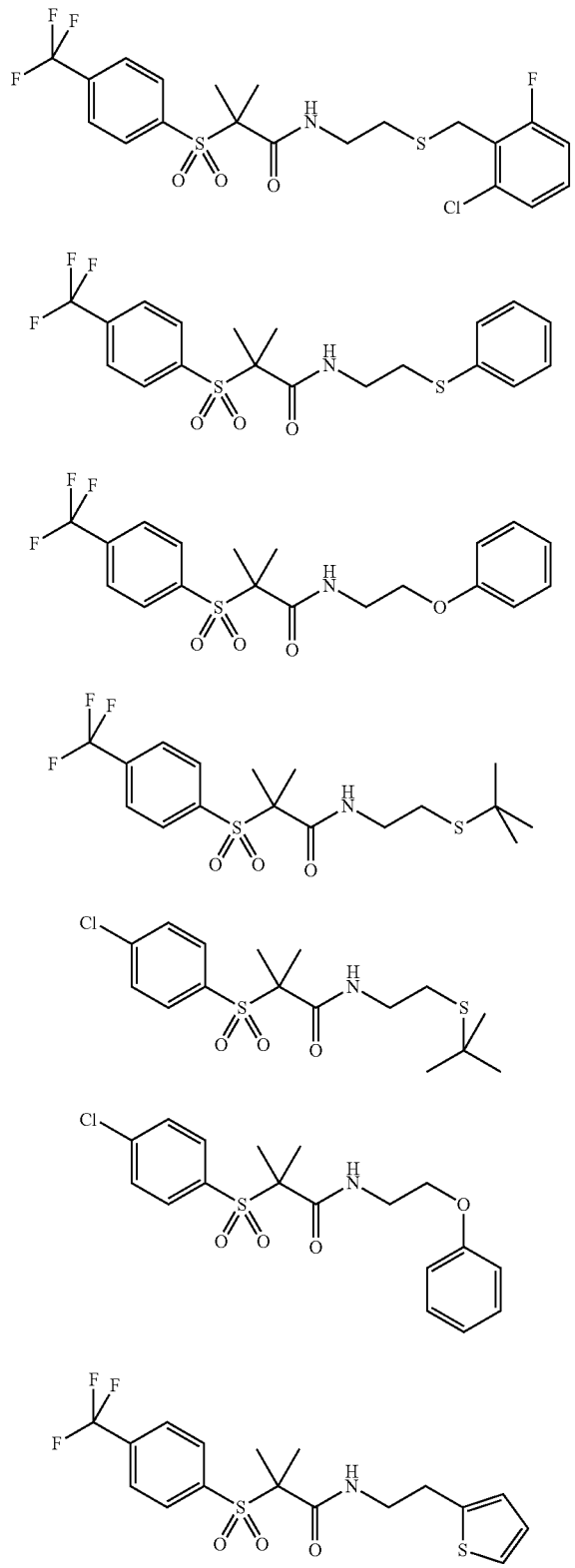
TABLE II-continued
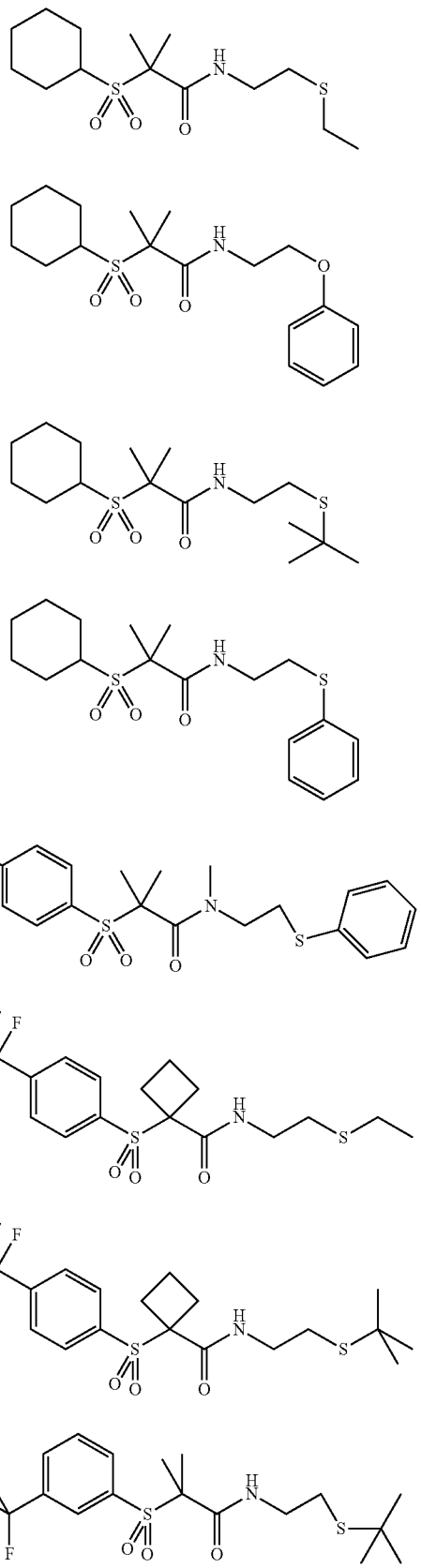

TABLE II-continued
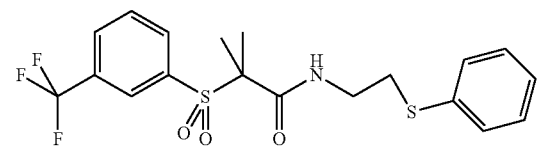 [SMILES: CC(C)(C(=O)NCCSc1ccccc1)S(=O)(=O)c1cccc(C(F)(F)F)c1]
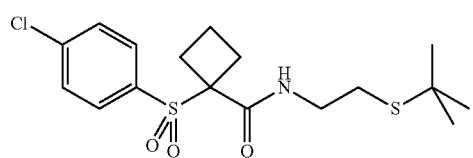 [SMILES: CC(C)(C)SCCNC(=O)C1(S(=O)(=O)c2ccc(Cl)cc2)CCC1]
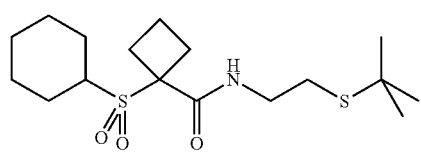 [SMILES: CC(C)(C)SCCNC(=O)C1(S(=O)(=O)C2CCCCC2)CCC1]
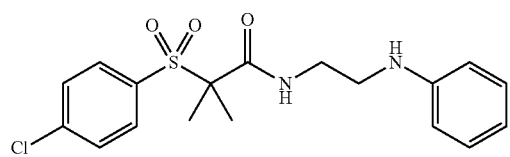 [SMILES: CC(C)(C(=O)NCCNc1ccccc1)S(=O)(=O)c1ccc(Cl)cc1]
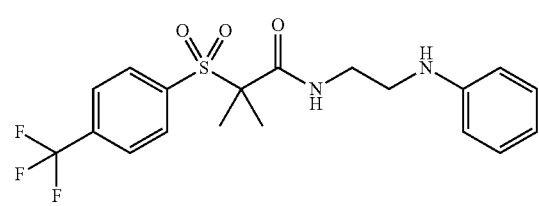 [SMILES: CC(C)(C(=O)NCCNc1ccccc1)S(=O)(=O)c1ccc(C(F)(F)F)cc1]
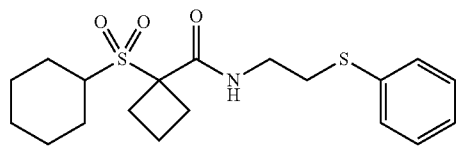 [SMILES: O=C(NCCSc1ccccc1)C1(S(=O)(=O)C2CCCCC2)CCC1]
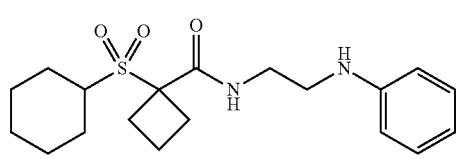 [SMILES: O=C(NCCNc1ccccc1)C1(S(=O)(=O)C2CCCCC2)CCC1]
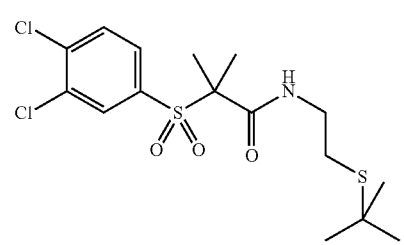 [SMILES: CC(C)(C)SCCNC(=O)C(C)(C)S(=O)(=O)c1ccc(Cl)c(Cl)c1]
TABLE II-continued
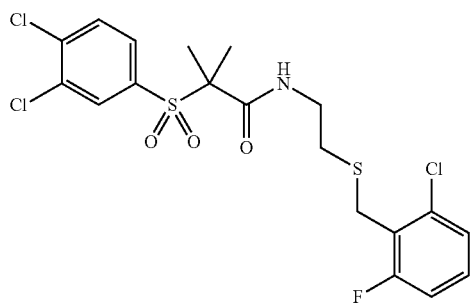 [SMILES: CC(C)(C(=O)NCCSCc1c(F)cccc1Cl)S(=O)(=O)c1ccc(Cl)c(Cl)c1]
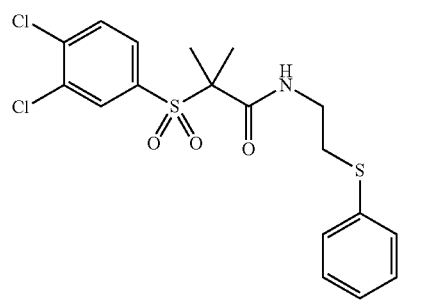 [SMILES: CC(C)(C(=O)NCCSc1ccccc1)S(=O)(=O)c1ccc(Cl)c(Cl)c1]
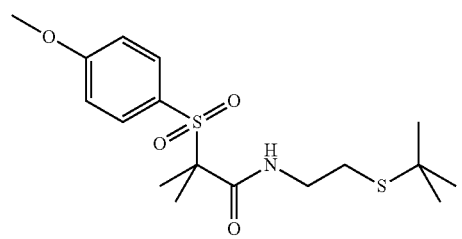 [SMILES: COc1ccc(S(=O)(=O)C(C)(C)C(=O)NCCSC(C)(C)C)cc1]
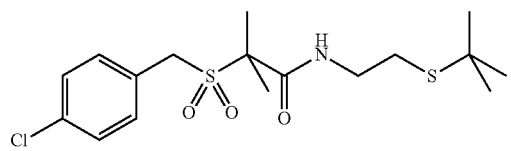 [SMILES: CC(C)(C)SCCNC(=O)C(C)(C)S(=O)(=O)Cc1ccc(Cl)cc1]
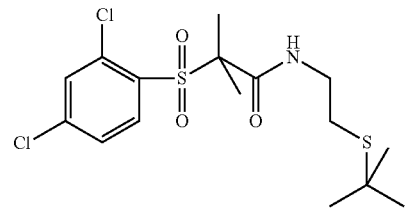 [SMILES: CC(C)(C)SCCNC(=O)C(C)(C)S(=O)(=O)c1ccc(Cl)cc1Cl]
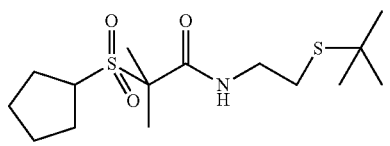 [SMILES: CC(C)(C)SCCNC(=O)C(C)(C)S(=O)(=O)C1CCCC1]
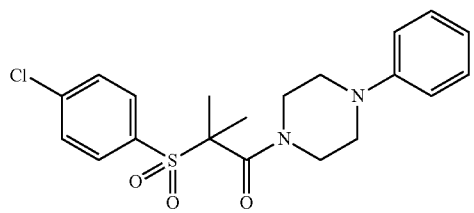 [SMILES: CC(C)(C(=O)N1CCN(c2ccccc2)CC1)S(=O)(=O)c1ccc(Cl)cc1]

TABLE II-continued
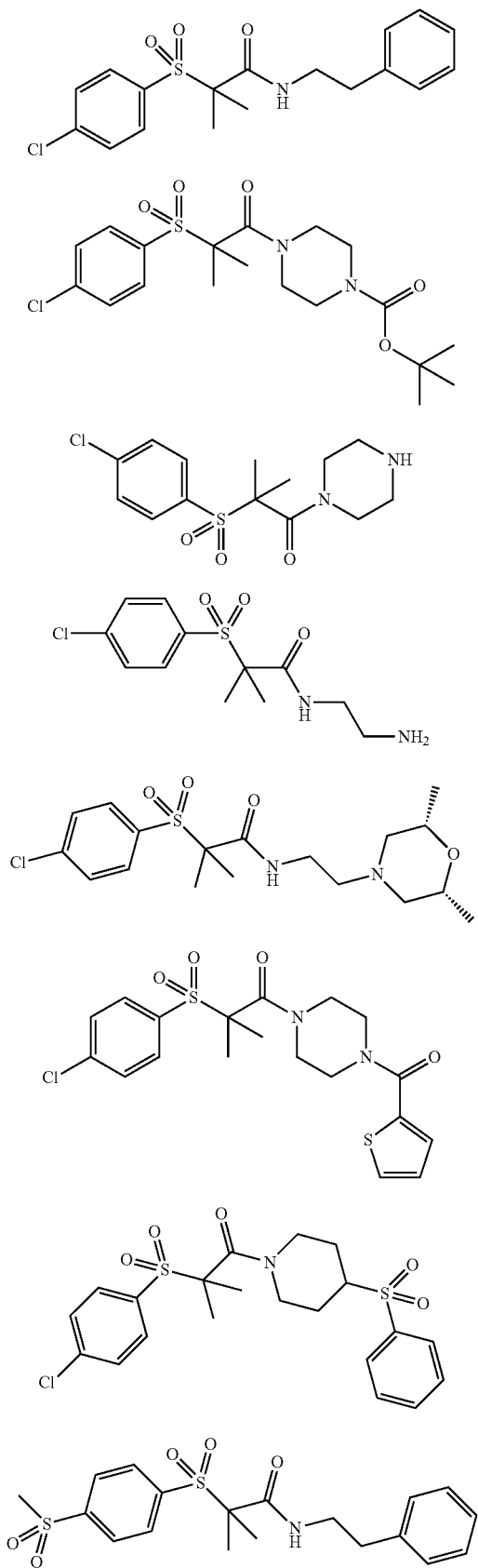
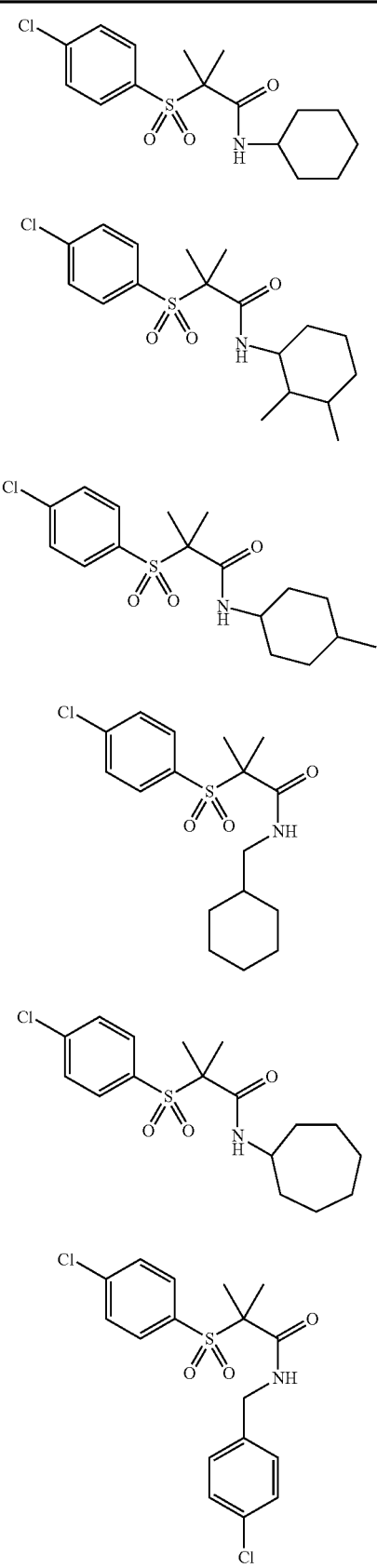

TABLE II-continued
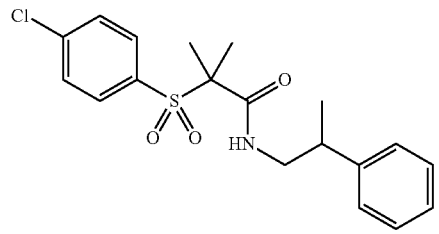 [SMILES: CC(CNC(=O)C(C)(C)S(=O)(=O)c1ccc(Cl)cc1)c1ccccc1]
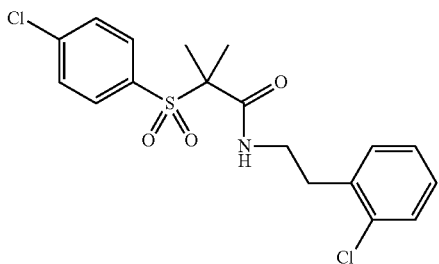 [SMILES: CC(C)(C(=O)NCCc1ccccc1Cl)S(=O)(=O)c1ccc(Cl)cc1]
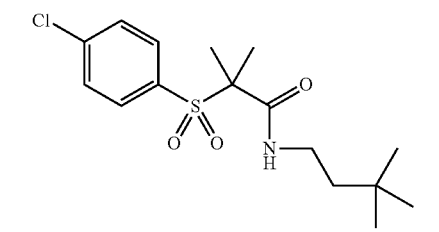 [SMILES: CC(C)(C)CCNC(=O)C(C)(C)S(=O)(=O)c1ccc(Cl)cc1]
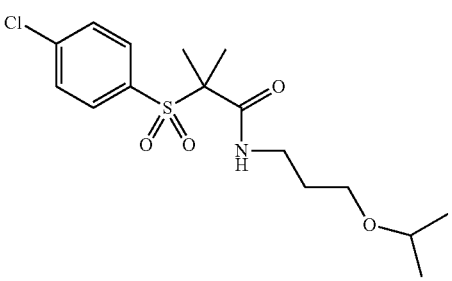 [SMILES: CC(C)OCCCNC(=O)C(C)(C)S(=O)(=O)c1ccc(Cl)cc1]
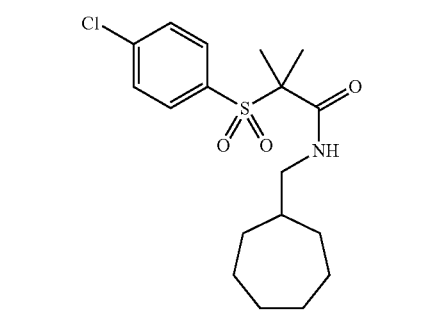 [SMILES: CC(C)(C(=O)NCC1CCCCCC1)S(=O)(=O)c1ccc(Cl)cc1]
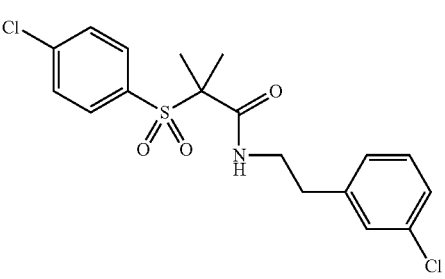 [SMILES: CC(C)(C(=O)NCCc1cccc(Cl)c1)S(=O)(=O)c1ccc(Cl)cc1]
TABLE II-continued
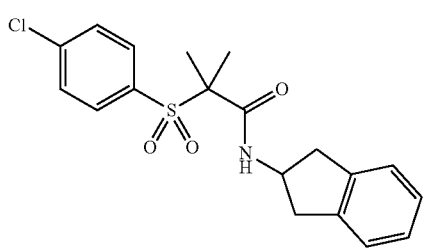 [SMILES: CC(C)(C(=O)NC1Cc2ccccc2C1)S(=O)(=O)c1ccc(Cl)cc1]
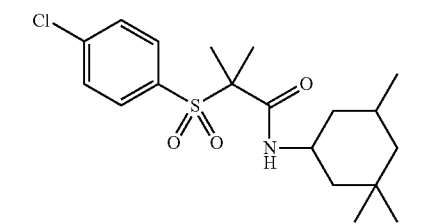 [SMILES: CC1CC(NC(=O)C(C)(C)S(=O)(=O)c2ccc(Cl)cc2)CC(C)(C)C1]
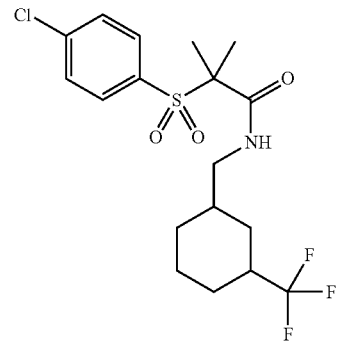 [SMILES: CC(C)(C(=O)NCC1CCCC(C(F)(F)F)C1)S(=O)(=O)c1ccc(Cl)cc1]
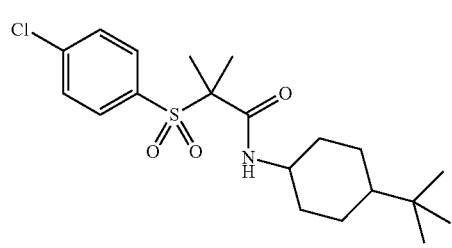 [SMILES: CC(C)(C)C1CCC(NC(=O)C(C)(C)S(=O)(=O)c2ccc(Cl)cc2)CC1]
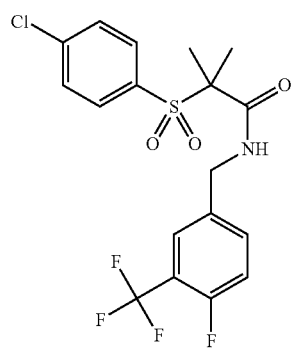 [SMILES: CC(C)(C(=O)NCc1ccc(F)c(C(F)(F)F)c1)S(=O)(=O)c1ccc(Cl)cc1]

TABLE II-continued
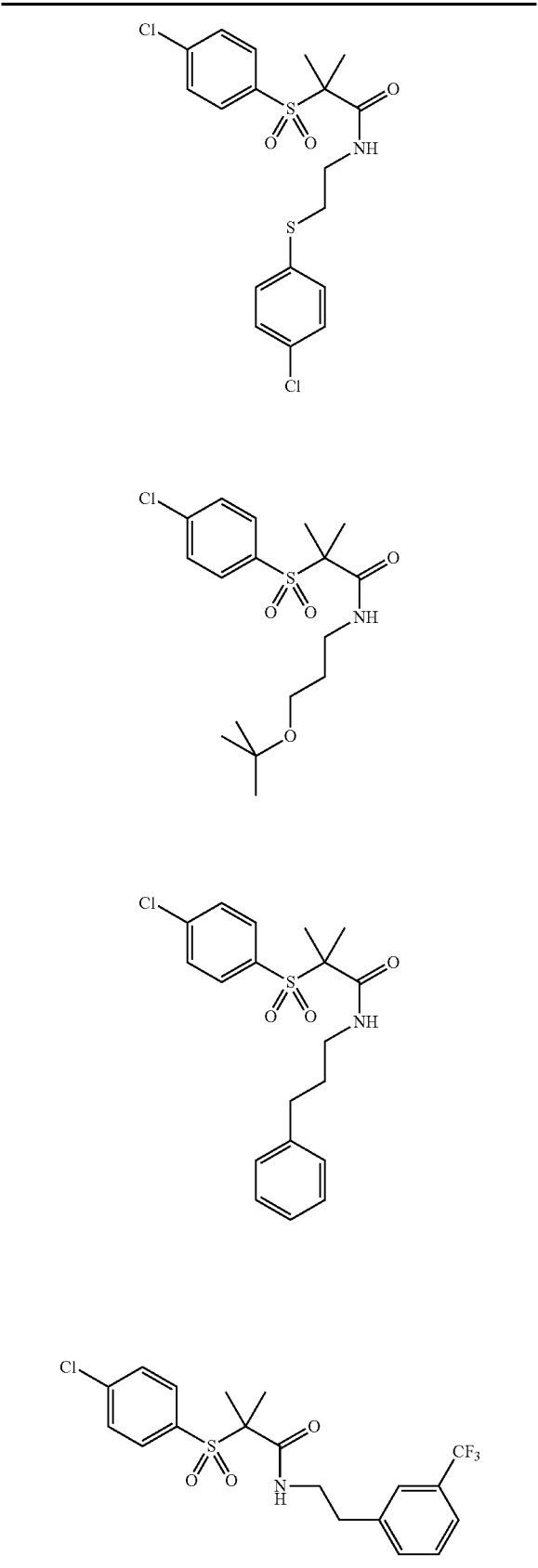
TABLE II-continued
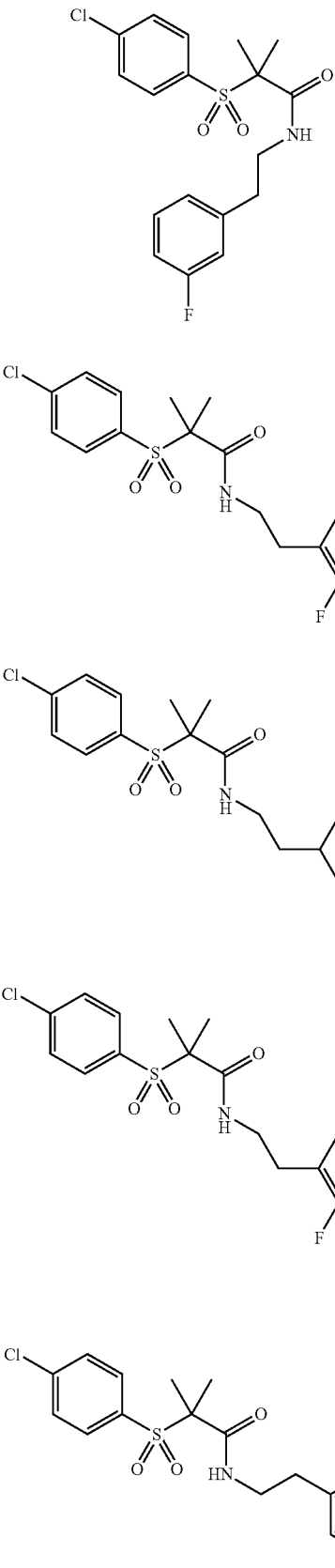

TABLE II-continued

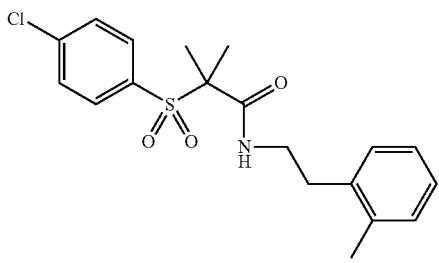 [SMILES: Cc1ccccc1CCNC(=O)C(C)(C)S(=O)(=O)c1ccc(Cl)cc1]

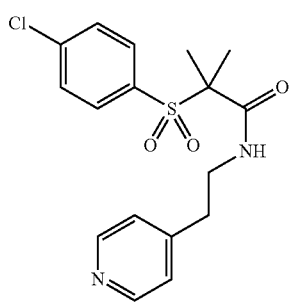 [SMILES: CC(C)(C(=O)NCCc1ccncc1)S(=O)(=O)c1ccc(Cl)cc1]

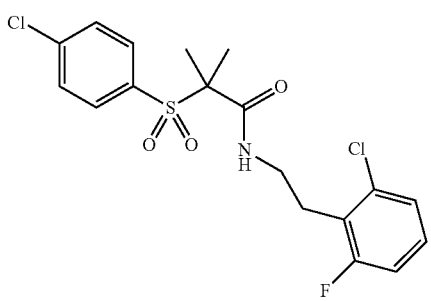 [SMILES: CC(C)(C(=O)NCCc1c(F)cccc1Cl)S(=O)(=O)c1ccc(Cl)cc1]

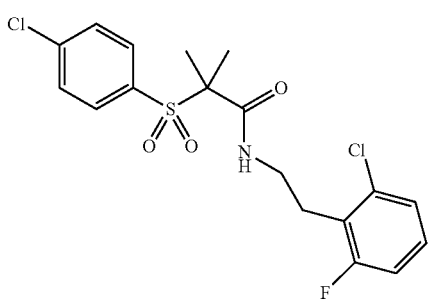 [SMILES: CC(C)(C(=O)NCCc1c(F)cccc1Cl)S(=O)(=O)c1ccc(Cl)cc1]

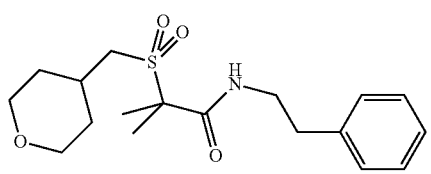 [SMILES: CC(C)(C(=O)NCCc1ccccc1)S(=O)(=O)CC1CCOCC1]

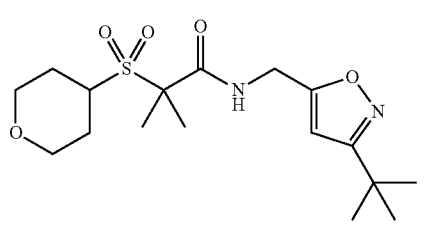 [SMILES: CC(C)(C)c1cc(CNC(=O)C(C)(C)S(=O)(=O)C2CCOCC2)on1]

TABLE II-continued

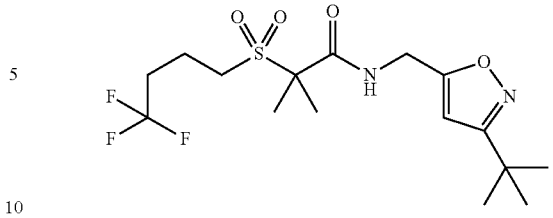

or a pharmaceutically acceptable salt thereof.

In all the compounds disclosed hereinabove in this application, in the event the nomenclature is in conflict with the structure, it shall be understood that the compound is defined by the structure.

The invention also relates to pharmaceutical preparations, containing as active substance one or more compounds of formula (I), or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles or cycloalkyls include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 3-10 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-10 membered monocyclic or 8-11 membered bicyclic ring containing 1-4 heteroatoms such as N, O and S.

Unless otherwise stated, heterocycles and heteroaryl include but are not limited to, for example benzoxazolyl, benzothiazolyl, benzimidazolyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, triazolyl, thiomorpholinyl, 1,1-Dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, thieno[2,3-d]pyrimidinyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle.

Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydronaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine, preferably fluorine and chlorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1$-$C_4$ alkyl$)_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I) and (IA). In all methods, unless specified otherwise, R, $R^1$, $R^2$, $R^3$, $R^4$, $R^5$, $R^6$ and n the formulas below shall have the meaning of R, $R^1$, $R^2$, $R^3$, $R^4$, $R^5$, $R^6$ and n in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art. Synthetic methods disclosed in WO2008098025, WO2008014199, WO2008039645, and WO2009061652 may also be used in preparing compounds of the invention.

Compounds of Formula (I) and (IA) may be synthesized by the method illustrated in Scheme 1

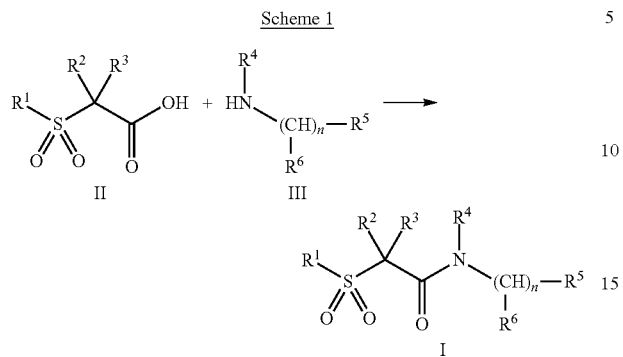

As shown in scheme 1, reacting the acid of formula II with a reagent such as thionyl chloride or oxalyl chloride, provides the acid chloride which is then reacted with an amine of formula III, in a suitable solvent, in the presence of a suitable base, to provide a compound of formula (I). Alternatively, the acid of formula II may also be coupled with an amine of formula III under standard coupling conditions, to provide a compound of formula (I). Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine.

Further modification of the initial product of formula (I) by methods known in the art and illustrated in the Examples below, may be used to prepare additional compounds of this invention.

Intermediate acid II may be made by the method outlined in Scheme 2

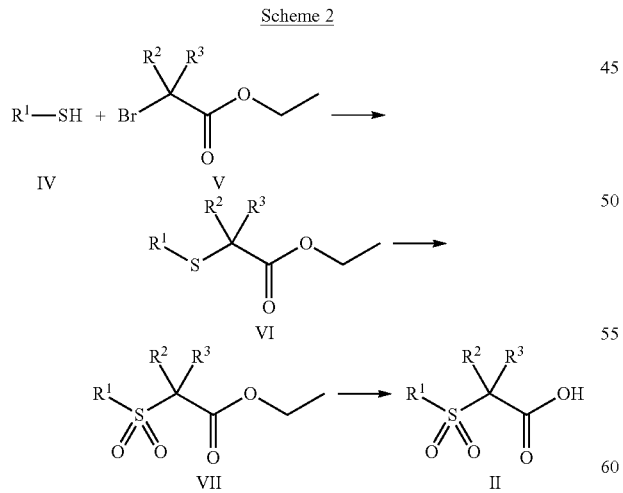

As illustrated in above, reaction of a thiol of formula IV with a bromo ethyl ester of formula V, in a suitable solvent, in the presence of a suitable base, provides a thioether of formula VI. Reacting the thioether of formula VI with a suitable oxidizing agent provides the corresponding sulfone of formula VII. Hydrolysis of the ester group of sulfone of formula VII, in a suitable solvent, in the presence of a suitable base such as lithium hydroxide, provides the corresponding acid of formula II.

Intermediate acid II may also be made by the method outlined in Scheme 3

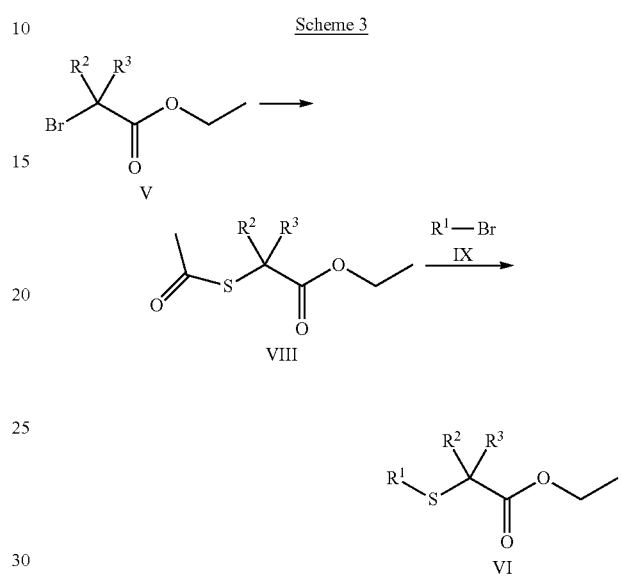

Reaction of the starting bromoester of formula V with a reagent such as potassium thioacetate, in a suitable solvent, provides a thioacetic acid ester of formula VIII. Reaction of the thioacetic acid ester VIII with a bromide of formula IX, in a suitable solvent in the presence of a suitable base, provides the corresponding sulfanyl acid ethyl ester of formula VI. The sulfanyl acid ethyl ester of formula VI may be converted to intermediate acid of formula II by the sequence of steps shown in scheme 2.

Intermediate acid II may be made by the method outlined in Scheme 4

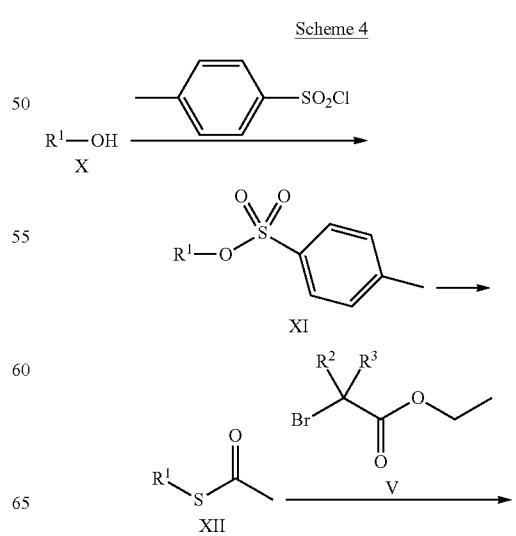

-continued

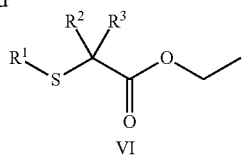

VI

As illustrated in scheme 4, reaction of an alcohol of formula X with p-toluenesulfonyl chloride, in a suitable solvent, in the presence of a suitable base, provides the sulfonic acid ester of formula XI. Reaction of the compound of formula XI with potassium thioacetate, in a suitable solvent, provides a compound of formula XII. Reaction of the intermediate of formula XII with the bromoester of formula V, in a suitable solvent, in the presence of a suitable base, provides the intermediate of formula VI which may be converted to the desired intermediate acid of formula II by the reaction sequence shown in scheme 2.

Intermediate acid II may also be made by the method outlined in Scheme 5

Scheme 5

As shown in scheme 5, sulfonyl chloride of formula XIII is converted to the corresponding sulfinic acid sodium salt of formula XIV, using procedures reported in the literature. Reaction of the sulfinic acid sodium salt of formula XIV with a bromoester of formula V in a suitable solvent, provides a sulfone ester of formula VII. Hydrolysis of the sulfone ester of formula VII provides the intermediate acid of formula II.

SYNTHETIC EXAMPLES

The manner in which the compounds of the invention can be made will be further understood by way of the following Examples.

Acid Method A:

Acids of method A are prepared as described in WO2008039645, Boehringer Ingelheim International GmbH. or as described in WO2008014199, Boehringer Ingelheim International GmbH.

Synthesis of 2-Cyclopentanesulfonyl-2-methyl-propionic acid

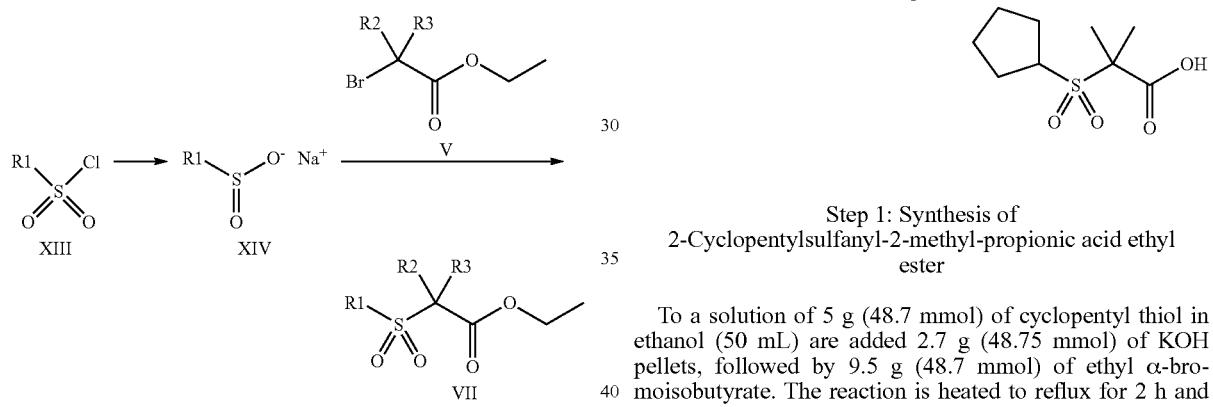

Step 1: Synthesis of 2-Cyclopentylsulfanyl-2-methyl-propionic acid ethyl ester

To a solution of 5 g (48.7 mmol) of cyclopentyl thiol in ethanol (50 mL) are added 2.7 g (48.75 mmol) of KOH pellets, followed by 9.5 g (48.7 mmol) of ethyl α-bromoisobutyrate. The reaction is heated to reflux for 2 h and then cooled to room temperature. The solid (KBr) is separated by filtration and rinsed with ethanol (20 mL). The filtrate is concentrated under reduced pressure and the residue dissolved in DCM (50 mL). The organic layer is washed with saturated aqueous $NaHCO_3$ solution (50 mL). The aqueous washes are back-extracted with DCM (10 mL). The combined organics are washed with brine, dried over $Na_2SO_4$. Filtration and concentration under reduced pressure affords 8.1 g of 2-cyclopentylsulfanyl-2-methyl-propionic acid ethyl ester. Yield: 77%, ES-MS: m/z 217 [M+H]

According to this procedure the following thioethers are synthesized with the following modifications to be noted: for the acids, which are used to synthesize examples 13-14, 17-18 and 21-22, ethyl-1-bromocyclobutane carboxylate is used instead of ethyl α-bromoisobutyrate.

TABLE 1

| Structure | $^1$H-NMR | Yield [%] | m/z [M + H] |
|---|---|---|---|
| 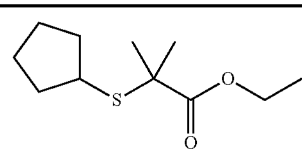 | (250 MHz, CHLOROFORM-d) δ ppm 1.29 (3 H, t, J = 7.14 Hz), 1.36-1.77 (12 H, m), 1.95-2.13 (2 H, m), 3.08-3.26 (1 H, m), 4.18 (2 H, q, J = 7.14 Hz) | 77 | 217 |

TABLE 1-continued

| Structure | ¹H-NMR | Yield [%] | m/z [M + H] |
|---|---|---|---|
| 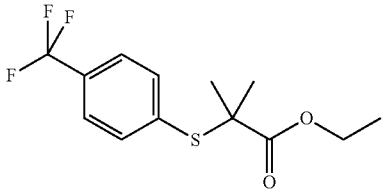 [SMILES: CCOC(=O)C(C)(C)Sc1ccc(C(F)(F)F)cc1] | (250 MHz, CHLOROFORM-d) δ ppm 1.66 (6 H, s), 7.84 (2 H, d, J = 8.23 Hz), 8.05 (2 H, d, J = 8.14 Hz) | 99 | 293 |
| 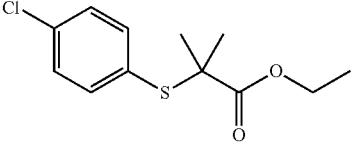 [SMILES: CCOC(=O)C(C)(C)Sc1ccc(Cl)cc1] | (400 MHz, CHLOROFORM-d) δ ppm 1.23 (3 H, t, J = 7.21 Hz), 1.48 (6 H, s), 4.12 (2 H, q, J = 7.09 Hz), 7.28-7.33 (2 H, m), 7.37-7.43 (2 H, m) | 79 | 259 |
| 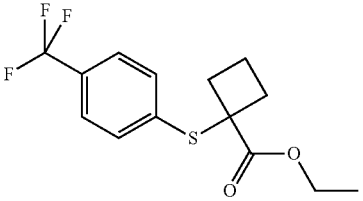 [SMILES: CCOC(=O)C1(Sc2ccc(C(F)(F)F)cc2)CCC1] | (400 MHz, CHLOROFORM-d) δ ppm 1.19 (3 H, t, J = 7.09 Hz), 1.91-2.05 (1 H, m), 2.21-2.34 (3 H, m), 2.73-2.84 (2 H, m), 4.16 (2 H, q, J = 7.09 Hz), 7.38-7.43 (2 H, m), 7.51 (2 H, d, J = 8.31 Hz) | 94 | 305 |
| 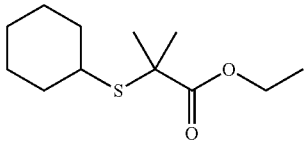 | (250 MHz, CHLOROFORM-d) δ ppm 1.16-1.42 (9 H, m), 1.49 (6 H, s), 1.58-1.78 (2 H, m), 1.81-1.91 (2 H, m), 2.67-2.91 (1 H, m), 4.15 (2 H, q, J = 7.14 Hz) | 84 | 231 |
| 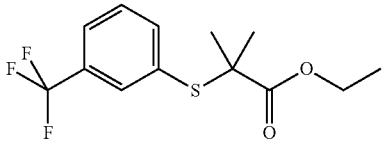 [SMILES: CCOC(=O)C(C)(C)Sc1cccc(C(F)(F)F)c1] | (250 MHz, CHLOROFORM-d) δ ppm 1.21 (3 H, t, J = 7.14 Hz), 1.51 (6 H, s), 4.11 (2 H, q, J = 7.14 Hz), 7.39-7.54 (1 H, m), 7.59-7.70 (2 H, m), 7.75 (1 H, s) | 83 | 293 |
| 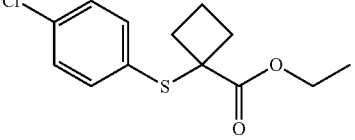 | (400 MHz, CHLOROFORM-d) δ ppm 1.15 (3 H, t, J = 7.21 Hz), 1.75-1.92 (1 H, m), 2.08-2.24 (3 H, m), 2.50-2.70 (2 H, m), 4.08 (2 H, q, J = 7.25 Hz), 7.12-7.31 (4 H, m) | 91 | 271 |
| 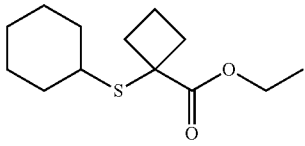 [SMILES: CCOC(=O)C1(SC2CCCCC2)CCC1] | Data not available | 68 | 243 |
| 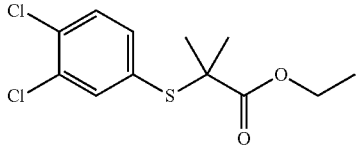 [SMILES: CCOC(=O)C(C)(C)Sc1ccc(Cl)c(Cl)c1] | (250 MHz, CHLOROFORM-d) δ ppm 1.25 (3 H, t, J = 7.14 Hz), 1.50 (6 H, s), 4.14 (2 H, q, J = 7.14 Hz), 7.24-7.34 (1 H, m), 7.35-7.44 (1 H, m), 7.57 (1 H, d, J = 2.01 Hz) | 100 | 293/ 295/ 297 |
| 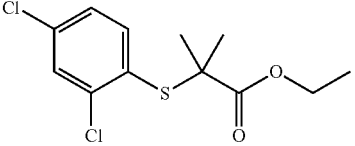 [SMILES: CCOC(=O)C(C)(C)Sc1ccc(Cl)cc1Cl] | (250 MHz, CHLOROFORM-d) δ ppm 1.25 (3 H, t, J = 7.14 Hz), 1.50 (6 H, s), 4.14 (2 H, q, J = 7.14 Hz), 7.24-7.34 (1 H, m), 7.35-7.44 (1 H, m), 7.57 (1 H, d, J = 2.01 Hz) | 87 | 293/ 295/ 297 |

TABLE 1-continued

| Structure | ¹H-NMR | Yield [%] | m/z [M + H] |
|---|---|---|---|
| (4-methoxyphenyl-S-C(CH₃)₂-C(O)-O-ethyl) | (400 MHz, CHLOROFORM-d) δ ppm 1.24 (3 H, t, J = 7.14 Hz), 1.46 (6 H, s), 3.82 (3 H, s), 4.12 (2 H, q, J = 7.14 Hz), 6.85 (2 H, d, J = 8.97 Hz), 7.40 (2 H, d, J = 8.96 Hz) | 92 | 255 |
| (4-chlorobenzyl-S-C(CH₃)₂-COOH) | Data not available | 40* | 245/247 |

*hydrolysis of the ethyl ester occurred during reaction conditions

Step 2: Synthesis of 2-Cyclopentanesulfonyl-2-methyl-propionic acid ethyl ester To a solution of 6 g (27.7 mmol) of 2-cyclopentylsulfanyl-2-methyl-propionic acid ethyl ester in 1,4-dioxane/water (4/1, 100 mL) are added in several portions 51.2 g (83 mmol) of potassium monopersulfate triple salt (OXONE®). The white suspension is stirred at room temperature for 3 h. The white solid is separated by filtration and washed with 1,4-dioxane (10 mL). The filtrate is concentrated under reduced pressure to remove the organic solvent. The resulting aqueous solution is extracted with DCM (3×40 mL). The combined organic extracts are washed with saturated aqueous NaHCO₃ solution, brine, dried over Na₂SO₄ and filtered. The filtrate is concentrated under reduced pressure to afford 5.4 g of 2-cyclopentanesulfonyl-2-methyl-propionic acid ethyl ester. Yield: 78%, ES-MS: m/z 249 [M+H]

According to this procedure the following sulfones are synthesized:

TABLE 2

| Structure | ¹H-NMR | Yield [%] | m/z [M + H] |
|---|---|---|---|
| cyclopentyl-SO₂-C(CH₃)₂-C(O)-O-ethyl | (400 MHz, CHLOROFORM-d) δ ppm 1.32 (3 H, t, J = 7.21 Hz), 1.55-1.70 (8 H, m), 1.71-1.86 (2 H, m), 1.96-2.20 (4 H, m), 3.83-3.96 (1 H, m), 4.25 (2 H, q, J = 7.09 Hz) | 78 | 249 |
| 4-(CF₃)phenyl-SO₂-C(CH₃)₂-C(O)-O-ethyl | (250 MHz, CHLOROFORM-d) δ ppm 1.15 (3 H, t, J = 7.14 Hz), 1.58 (6 H, s), 4.09 (2 H, q, J = 7.14 Hz), 7.73-7.82 (2 H, m), 7.96 (2 H, d, J = 8.23 Hz) | 84 | 325 |
| 4-Cl-phenyl-SO₂-C(CH₃)₂-C(O)-O-ethyl | (250 MHz, CHLOROFORM-d) δ ppm 1.22 (3 H, q, J = 7.17 Hz), 1.60 (6 H, s), 4.13 (2 H, q, J = 7.14 Hz), 7.51 (2 H, d, J = 8.51 Hz), 7.71-7.82 (2 H, m) | 86 | 291 |
| 4-(CF₃)phenyl-SO₂-cyclobutyl-C(O)-O-ethyl | (250 MHz, CHLOROFORM-d) δ ppm 1.18 (3 H, t, J = 7.14 Hz), 1.96-2.24 (2 H, m), 2.53-2.69 (2 H, m), 2.89-3.07 (2 H, m), 4.14 (2 H, q, J = 7.14 Hz), 7.81 (2 H, d, J = 8.23 Hz), 7.99 (2 H, d, J = 8.32 Hz) | 85 | 337 |

TABLE 2-continued

| Structure | ¹H-NMR | Yield [%] | m/z [M + H] |
|---|---|---|---|
| (cyclohexyl-SO₂-C(CH₃)₂-C(O)OEt) | (400 MHz, CHLOROFORM-d) δ ppm 1.08-1.38 (6 H, m), 1.48-1.72 (9 H, m), 1.83-1.95 (2 H, m), 2.11 (2 H, d, J = 13.94 Hz), 3.45-3.58 (1 H, m), 4.24 (2 H, q, J = 7.17 Hz) | 50 | 263 |
| (3-CF₃-phenyl-SO₂-C(CH₃)₂-C(O)OEt) | (400 MHz, CHLOROFORM-d) δ ppm 1.22 (3 H, t, J = 7.14 Hz), 1.65 (6 H, s), 4.15 (2 H, q, J = 7.14 Hz), 7.73 (1 H, t, J = 7.96 Hz), 7.94 (1 H, d, J = 9.15 Hz), 8.07 (1 H, d, J = 7.87 Hz), 8.13 (1 H, s) | 100 | 325 |
| (4-Cl-phenyl-SO₂-cyclobutyl-C(O)OEt) | (250 MHz, CHLOROFORM-d) δ ppm 1.21 (3 H, t, J = 7.14 Hz), 1.88-2.26 (2 H, m), 2.48-2.69 (2 H, m), 2.84-3.04 (2 H, m), 4.15 (2 H, q, J = 7.14 Hz), 7.52 (2 H, d, J = 8.78 Hz), 7.78 (2 H, d, J = 8.87 Hz) | 82 | 303/305 |
| (cyclohexyl-SO₂-cyclobutyl-C(O)OEt) | Data not available | 76 | 275 |
| (2,4-diCl-phenyl-SO₂-C(CH₃)₂-C(O)OEt) | (400 MHz, CHLOROFORM-d) δ ppm 1.24 (3 H, t, J = 7.09 Hz), 1.68 (6 H, s), 4.18 (2 H, q, J = 7.17 Hz), 7.44 (1 H, dd, J = 8.56, 1.96 Hz), 7.57 (1 H, d, J = 1.96 Hz), 7.95 (1 H, d, J = 8.56 Hz) | 30 | 325/327/329 |
| (2,4-diCl-phenyl-SO₂-C(CH₃)₂-C(O)OEt) | (400 MHz, CHLOROFORM-d) δ ppm 1.26 (3 H, t, J = 7.09 Hz), 1.63 (6 H, s), 4.18 (2 H, q, J = 7.09 Hz), 7.62-7.66 (1 H, m), 7.67-7.72 (1 H, m), 7.95 (1 H, d, J = 1.96 Hz) | 100 | 325/327/329 |
| (4-MeO-phenyl-SO₂-C(CH₃)₂-C(O)OEt) | (400 MHz, CHLOROFORM-d) δ ppm 1.12 (3 H, t, J = 7.14 Hz), 1.49 (6 H, s), 3.78 (3 H, s), 4.04 (2 H, q, J = 7.14 Hz), 6.89 (2 H, d, J = 8.97 Hz), 7.66 (2 H, d, J = 9.15 Hz) | 100 | 287 |
| (4-Cl-benzyl-SO₂-C(CH₃)₂-C(O)OH) | Data not available | 81* | 277/279, 294/296 [M + H₂O⁺] |

*2-(4-Chloro-benzylsulfanyl)-2-methyl-propionic acid used for oxidation step

Step 3: Synthesis of 2-Cyclopentanesulfonyl-2-methyl-propionic acid

To a solution of 5.4 g (21.7 mmol) of 2-cyclopentanesulfonyl-2-methyl-propionic acid ethyl ester in THF/water (4/1, 60 mL) are added 2.3 g (56.6 mmol) of lithium hydroxide monohydrate. The reaction is stirred at room temperature for 18 h. The reaction is further diluted with water (20 mL) and then washed with DCM (2×15 mL). The basic aqueous layer is cooled in an ice bath and then acidified with 2M aqueous HCl solution to pH 2. The acidic aqueous layer is extracted with 2-propanol/chloroform (1/4, 100 mL). The combined organic extracts are washed with brine, dried over $Na_2SO_4$ and filtered. Concentration of the filtrate under reduced pressure affords 4.34 g of 2-cyclopentanesulfonyl-2-methyl-propionic acid. Yield: 92%, ES-MS: m/z 221 [M+H]

According to this procedure the following acids are synthesized:

TABLE 3

| Structure | ¹H-NMR | Yield [%] | m/z [M + H] |
|---|---|---|---|
| cyclopentyl-SO₂-C(CH₃)₂-COOH | (400 MHz, CHLOROFORM-d) δ ppm 1.54-1.72 (8 H, m), 1.72-1.88 (2 H, m), 1.98-2.22 (4 H, m), 3.87-4.00 (1 H, m), 9.26 (1 H, br. s.) | 92 | 221 |
| 4-(trifluoromethyl)phenyl-SO₂-C(CH₃)₂-COOH | (250 MHz, CHLOROFORM-d) δ ppm 1.66 (6 H, s), 7.84 (2 H, d, J = 8.23 Hz), 8.05 (2 H, d, J = 8.14 Hz) | 75 | 297 |
| 4-chlorophenyl-SO₂-C(CH₃)₂-COOH | (250 MHz, CHLOROFORM-d) δ ppm 1.64 (6 H, s), 7.56 (2 H, d, J = 8.87 Hz), 7.84 (2 H, d, J = 8.87 Hz) | 60 | 263 |
| 4-(trifluoromethyl)phenyl-SO₂-cyclobutyl-COOH | (400 MHz, CHLOROFORM-d) δ ppm 2.00-2.27 (2 H, m), 2.57-2.71 (2 H, m), 2.92-3.04 (2 H, m), 7.82 (2 H, d, J = 8.23 Hz), 8.04 (2 H, d, J = 8.23 Hz) | 75 | 309, 326 [M + H₂O] |
| cyclohexyl-SO₂-C(CH₃)₂-COOH | (250 MHz, CHLOROFORM-d) δ ppm 1.11-1.49 (3 H, m), 1.53-1.79 (9 H, m), 1.85-2.00 (2 H, m), 2.06-2.22 (2 H, m), 3.37-3.56 (1 H, m) | 64 | 257 [M + Na] |
| 3-(trifluoromethyl)phenyl-SO₂-C(CH₃)₂-COOH | (400 MHz, CHLOROFORM-d) δ ppm 1.66 (6 H, s), 7.74 (1 H, t, J = 7.87 Hz), 7.96 (1 H, d, J = 8.42 Hz), 8.11 (1 H, d, J = 8.05 Hz), 8.15 (1 H, s) | 89 | 314 [M + H₂O] |
| 4-chlorophenyl-SO₂-cyclobutyl-COOH | (400 MHz, CHLOROFORM-d) δ ppm 1.98-2.23 (2 H, m), 2.56-2.68 (2 H, m), 2.89-3.01 (2 H, m), 7.53 (2 H, d, J = 8.78 Hz), 7.83 (2 H, d, J = 8.60 Hz), 8.85 (1 H, br. s.) | 95 | 275, 292 [M + H₂O] |
| cyclohexyl-SO₂-cyclobutyl-COOH | Data not available | 89 | 247 |
| 3,4-dichlorophenyl-SO₂-C(CH₃)₂-COOH | (400 MHz, CHLOROFORM-d) δ ppm 1.66 (6 H, s), 7.63-7.69 (1 H, m), 7.71-7.77 (1 H, m), 7.99 (1 H, d, J = 2.20 Hz) | 74 | 297/299, 314/316/318 [M + H₂O] |

TABLE 3-continued

| Structure | ¹H-NMR | Yield [%] | m/z [M + H] |
|---|---|---|---|
| Cl-C6H3(Cl)-SO2-C(CH3)2-COOH (2,4-dichlorophenyl) | (400 MHz, CHLOROFORM-d) d ppm 1.70 (6 H, s), 7.45 (1 H, dd, J = 8.56, 1.96 Hz), 7.58 (1 H, d, J = 2.20 Hz), 7.99 (1 H, d, J = 8.56 Hz) | 90 | 314/316 [M + H2O] |
| MeO-C6H4-SO2-C(CH3)2-COOH | (400 MHz, CHLOROFORM-d) δ ppm 1.62 (6 H, s), 3.90 (3 H, s), 7.02 (2 H, d, J = 8.96 Hz), 7.81 (2 H, d, J = 8.97 Hz) | 92 | 259 |

Acid Method B:

Acids of method B are prepared by adaptation of the synthetic method described in WO2008039645, Boehringer Ingelheim International GmbH.

Synthesis of 2-Methyl-2-(tetrahydro-pyran-4-yl-methanesulfonyl)-propionic acid

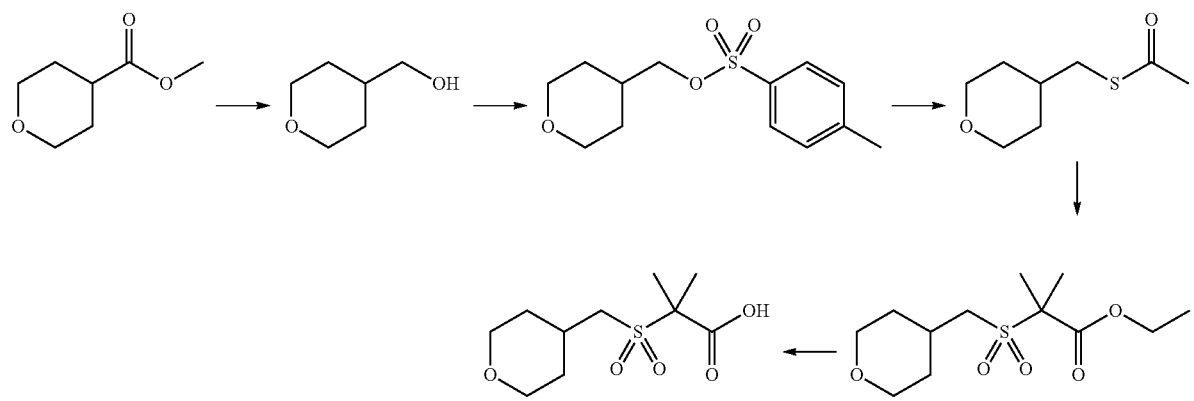

Step 1: Synthesis of (Tetrahydro-pyran-4-yl)-methanol

To a solution of 250 mL of LiAlH$_4$ (2.3M solution in THF, 0.575 mol) in THF (200 mL) is added dropwise a solution of 130 mL (0.974 mol) of tetrahydro-pyran-4-carboxylic acid methyl ester in THF (900 mL) under nitrogen atmosphere (CAUTION: highly exothermic reaction!). The temperature is kept at 40-45° C. with an ice-bath. Upon complete addition, the reaction is stirred at room temperature for 1.5 h. The reaction is cooled in an ice-bath and quenched with addition of water (22 mL), 15% aqueous NaOH solution (21 mL) and water (66 mL). The resulting precipitate is removed by filtration through Celite® and is rinsed with THF (300 mL). The filtrate is concentrated under reduced pressure to afford 102.5 g of (tetrahydro-pyran-4-yl)-methanol as a colorless oil. Yield: 91%; ¹H NMR (400 MHz, CHLOROFORM-d) δ ppm 1.20-1.39 (2 H, m), 1.56-1.83 (3 H, m), 2.03 (1 H, br. s.), 3.29-3.52 (4 H, m), 3.89-4.05 (2 H, m)

Step 2: Synthesis of toluene-4-sulfonic acid tetrahydro-pyran-4-ylmethyl ester Prepared as described by adaptation of the following literature reference:

Radziszewski, J. G. et al. *J. Am. Chem. Soc.* 1993, 115, 8401.

To a solution of 97 g (810 mmol) of (tetrahydro-pyran-4-yl)-methanol in 2-methyltetrahydrofuran (190 mL) are added 165 mL of 50% aqueous NaOH solution. To this stirred suspension is added dropwise with cooling a solution of p-toluene-sulfonylchloride (283 g, 1.46 mol) in 2-methyltetrahydrofuran (280 mL). The reaction is stirred at 30-35° C. for 18h. The suspension is poured into a mixture of ice-water (280 mL) and aqueous HCl solution (37%, 203 mL). After addition of methylcyclohexane (1.4 L) and further ice-water (0.2 L), the reaction mixture is stirred for 2 h in an ice-bath. The resulting crystalline precipitate is isolated by filtration and washed with methylcyclohexane (0.5 L) and water (0.5 L). Drying under reduced pressure at 40° C. gave 216 g of toluene-4-sulfonic acid tetrahydro-pyran-4-ylmethyl ester as white crystalline solid. Yield: 99%, ES-MS: m/z 271 [M+H]; ¹H NMR (400 MHz, CHLOROFORM-d) δ ppm 1.19-1.35 (2 H, m), 1.54-1.63 (2 H, m), 1.85-2.02 (1 H, m), 2.45 (3 H, s), 3.28-3.39 (2 H, m), 3.86 (2 H, d, J=6.60 Hz), 3.93 (2 H, dd, J=11.37, 4.52 Hz), 7.35 (2 H, d, J=9.29 Hz), 7.78 (2 H, d, J=8.31 Hz)

Step 3: Synthesis of Thioacetic acid S-(tetrahydro-pyran-4-ylmethyl)ester

Prepared as described by adaptation of the following literature reference:
Watson, R. J. et al. *Tetrahedron Lett.* 2002, 43, 683-685.

To a solution of 224 g (0.83 mol) of toluene-4-sulfonic acid tetrahydro-pyran-4-ylmethyl ester in methyl isobutylketone (1.6 L) are added 189 g (1.66 mol) of potassium thioacetate. The beige suspension is stirred at 70° C. for 4.5 h. The reaction mixture is cooled to room temperature and water (1.8 L) is added. The organic layer is washed with 10% aqueous $K_2CO_3$ solution (1.8 L) and water (1 L). The organic layer is filtered through Celite® (20 g), activated charcoal (20 g) and $Na_2SO_4$ (20 g) and the filtrate is concentrated under reduced pressure. The residual oil is azeotroped with methylcyclohexane (200 mL) and n-heptanes (250 mL) to afford 138 g of thioacetic acid S-(tetrahydro-pyran-4-ylmethyl)ester as a yellow-orange oil (CAUTION: Stench!). Yield: 96%; ES-MS: m/z 175 [M+H]; $^1$H NMR (400 MHz, CHLOROFORM-d) δ ppm 1.23-1.40 (2 H, m), 1.59-1.78 (3 H, m), 2.33 (3 H, d, J=4.16 Hz), 2.82 (2 H, dd, J=6.24, 3.79 Hz), 3.27-3.39 (2 H, m), 3.88-4.02 (2 H, m)

Step 4: Synthesis of 2-Methyl-2-(tetrahydro-pyran-4-ylmethanesulfonyl)-propionic acid ethyl ester A solution of 90 g (516 mmol) of thioacetic acid S-(tetrahydro-pyran-4-ylmethyl)ester in toluene (500 mL) under nitrogen atmosphere is cooled in an ice-bath. A solution of sodium ethoxide in ethanol (21%, 231 mL) is added and the reaction stirred for 50 min. Then 76 mL (516 mmol) of ethyl α-bromoisobutyrate are added and the reaction stirred for 1 h. To the reaction mixture are added glacial acetic acid (8.9 mL) and water (500 mL). The organic layer is separated and washed with water (500 mL). A 3-neck round bottom flask is charged with water (500 mL), Oxone® (477 g, 775 mmol) and tetrabutylammonium-hydrogensulfate (5 g, 15 mmol) and the organic layer is added. The biphasic reaction mixture is stirred for 2 d at room temperature. The solids are removed by filtration and the layers of the filtrate are separated. The organic layer is washed with water (2×500 mL). The solvent is removed under reduced pressure and further azeotroped with toluene to give 125 g of 2-methyl-2-(tetrahydro-pyran-4-ylmethanesulfonyl)-propionic acid ethyl ester. Yield: 87%; ES-MS: m/z 279 [M+H]; $^1$H NMR (250 MHz, CHLOROFORM-d) δ ppm 1.32 (3 H, t, J=7.16 Hz), 1.39-1.59 (2 H, m), 1.64 (6 H, s), 1.81-1.97 (2 H, m), 2.29-2.53 (1 H, m), 3.15 (2 H, d, J=6.55 Hz), 3.45 (2 H, dd, J=1.83, 0.30 Hz), 3.88-4.03 (2 H, m), 4.26 (2 H, d, J=7.16 Hz)

Step 5: Synthesis of 2-Methyl-2-(tetrahydro-pyran-4-ylmethanesulfonyl)-propionic acid Prepared as described by adaptation of Method A, step 3.
To a solution of 123 g (0.44 mol) of 2-methyl-2-(tetrahydro-pyran-4-ylmethanesulfonyl)-propionic acid ethyl ester in THF (450 mL) are added 663 mL of 2M aqueous sodium hydroxide solution (1.33 mol). The reaction is stirred at room temperature for 1 h. To the reaction mixture is added TBME (1.25 L) and the layers are separated. The aqueous layer is cooled in an ice bath and then acidified with 37% aqueous HCl solution (123 mL). The resulting precipitate is isolated by filtration, washed with water (200 mL) and dried under reduced pressure at 50° C. to afford 101 g of 2-methyl-2-(tetrahydro-pyran-4-ylmethanesulfonyl)-propionic acid as white crystalline solids. Yield: 91%; ES-MS: m/z 251 [M+H]; $^1$H NMR (400 MHz, DMSO-d6) δ ppm 1.31-1.45 (2 H, m), 1.49 (6 H, s), 1.70-1.79 (2 H, m), 2.13-2.28 (1 H, m), 3.24 (2 H, d, J=6.60 Hz), 3.28-3.38 (2 H, m), 3.76-3.85 (2 H, m), 13.65 (1 H, br. s.)

Acid Method C

Synthesis of 2-Methyl-2-(4,4,4-trifluoro-butane-1-sulfonyl)-propionic acid

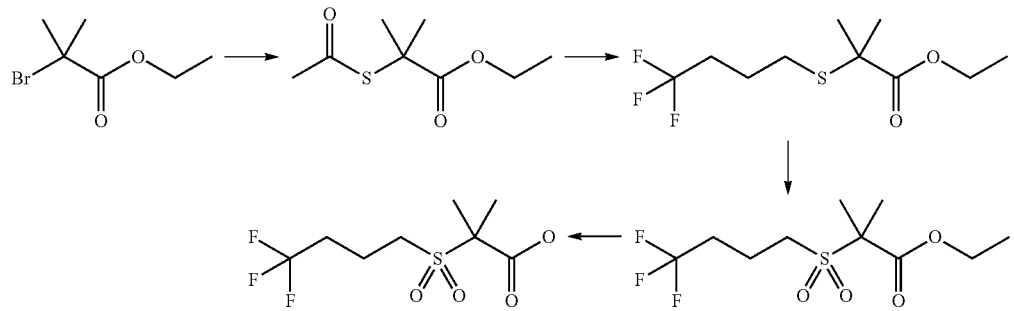

Step 1: Synthesis of 2-Acetylsulfanyl-2-methyl-propionic acid ethyl ester

To a solution of ethyl α-bromoisobutyrate (62 g, 0.32 mol) in DMF (500 mL) at room temperature is added potassium thioacetate (72 g, 0.63 mol). The reaction is stirred for 16 h and then concentrated under reduced pressure. The residue is diluted with a 2M aqueous hydrochloric acid solution (500 mL) and extracted with ethyl acetate (3×500 mL). The organic fractions are combined, washed with brine (300 mL), dried over $MgSO_4$, filtered and concentrated under reduced pressure. Purification by chromatography on silica eluting with heptanes/dichloromethane provides 44 g of 2-acetylsulfanyl-2-methyl-propionic acid ethyl ester. Yield: 73%; m/z 191 [M+H]; $^1$H NMR (250 MHz, CHLOROFORM-d) δ ppm 1.18-1.30 (3 H, m), 1.57 (6 H, s), 2.27 (3 H, s), 4.19 (2 H, q, J=7.16 Hz).

Step 1: Synthesis of 2-Methyl-2-(4,4,4-trifluoro-butylsulfanyl)-propionic acid ethyl ester To a solution of 149 g (785.4 mmol) of 2-acetylsulfanyl-2-methyl-propionic acid ethyl ester in ethanol (1.2 L, degassed under nitrogen for 1 h) are added 169.7 g (105 mmol) of sodium methoxide, followed by a solution of 150 g (785.4 mmol) of 1-bromo-4,4,4-trifluorobutane. The reaction is heated to 85° C. for 3 d. The solvent is removed under reduced pressure. The residue is dissolved in DCM (1 L) and washed with saturated aqueous NaHCO₃ solution (2×1 L). The organic layer is dried over Na₂SO₄, filtered and the filtrate is concentrated under reduced pressure to afford 171 g of 2-methyl-2-(4,4,4-trifluoro-butylsulfanyl)-propionic acid Yield: 93%; ES-MS: m/z 261 [M−H]. ¹H NMR (500 MHz, CHLOROFORM-d) δ ppm 1.71 (6 H, s), 2.18-2.28 (2 H, m), 2.30-2.42 (2 H, m), 3.38 (2 H, t, J=7.48 Hz), 6.96 (1 H, br. s.).

Acid Method D:

Synthesis of 2-Methyl-2-(tetrahydro-pyran-4-sulfonyl)-propionic acid

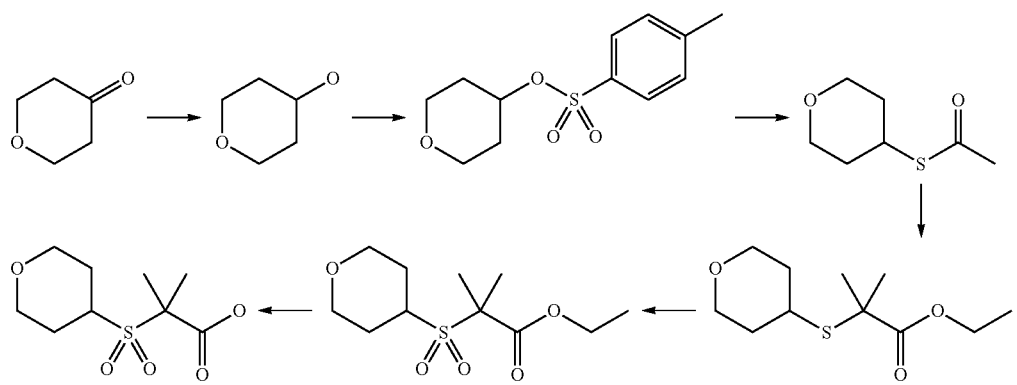

ethyl ester as a brown oil. Yield: 84%; ES-MS: m/z 259 [M+H]; ¹ H NMR (500 MHz, CHLOROFORM-d) δ ppm 1.29 (3 H, t, J=7.17 Hz), 1.51 (6 H, s), 1.76-1.86 (2 H, m), 2.12-2.27 (2 H, m), 2.69 (2 H, t, J=7.17 Hz), 4.18 (2 H, q, J=7.17 Hz).

Step 2: Synthesis of 2-Methyl-2-(4,4,4-trifluoro-butane-1-sulfonyl)-propionic acid ethyl ester To a solution of 220 g (851.7 mmol) of 2-methyl-2-(4,4,4-trifluoro-butylsulfanyl)-propionic acid ethyl ester in 1,4-dioxane/water (1/1, 4 L) are added 1047 g (1703.4 mmol) of Oxone® in portions over 0.5 h at room temperature. The reaction mixture is stirred at room temperature for 18 h. The solid is removed by filtration and rinsed with 1,4-dioxane (0.5 L). The filtrate is concentrated under reduced pressure to remove the organic solvent. The aqueous residue is extracted with DCM (2×1 L). The combined organic extracts are washed with saturated aqueous NaHCO₃ solution (2 L), dried over Na₂SO₄ and filtered. The filtrate is concentrated under reduced pressure to afford 226 g of 2-methyl-2-(4,4,4-trifluoro-butane-1-sulfonyl)-propionic acid ethyl ester as dark yellow oil. Yield 92%; ES-MS: m/z 291 [M+H]; ¹H NMR (500 MHz, CHLOROFORM-d) δ ppm 1.32 (3 H, t, J=7.17 Hz), 1.66 (6 H, s), 2.20 (2 H, quin, J=7.59 Hz), 2.28-2.41 (2 H, m), 3.34 (2 H, t, J=7.48 Hz), 4.27 (2 H, q, J=7.17 Hz).

Step 3: Synthesis of 2-Methyl-2-(4,4,4-trifluoro-butane-1-sulfonyl)-propionic acid To a solution of 170 g (585.6 mmol) of 2-methyl-2-(4,4,4-trifluoro-butane-1-sulfonyl)-propionic acid ethyl ester in THF (3.4 L) are added 225.4 g (1756.8 mmol) of potassium trimethylsilanolate in portions over 0.5 h. The reaction is stirred at room temperature for 18 h. The reaction mixture is acidified with 2M aqueous HCl solution (2 L) to pH 2 and extracted with DCM (2×2 L). The combined organic extracts are dried (Na₂SO₄) and filtered. The filtrate is concentrated under reduced pressure to afford 143 g of 2-methyl-2-(4,4,4-trifluoro-butane-1-sulfonyl)-propionic acid as yellow solids.

Step 1: Synthesis of Tetrahydro-pyran-4-ol

To a solution of 75 g (0.75 mol) of Tetrahydro-pyran-4-one in THF (150 mL) is added a suspension of 28.4 g (0.75 mol) LiAlH₄ in THF (600 mL) under nitrogen atmosphere maintaining the temperature below 30° C. with the aid of an ice-bath. Then the reaction is allowed to warm to room temperature and stirred for 5 h. The reaction is quenched by addition of saturated aqueous NH₄Cl solution until effervescence ceased. The resulting precipitate is removed by filtration through Celite® and washed with THF (150 mL). The filtrate is concentrated under reduced pressure to afford 71.1 g of tetrahydro-pyran-4-ol as a pale yellow oil. Yield: 92%, ¹H NMR (500 MHz, CHLOROFORM-d) δ ppm 1.54 (2 H, m), 1.81-1.92 (2 H, m), 2.11 (1 H, br. s.), 3.38-3.47 (2 H, m), 3.83 (1 H, tt, J=9.10, 4.38 Hz), 3.94 (2 H, dt, J=11.88, 4.15 Hz).

Step 2: Synthesis of Toluene-4-sulfonic acid tetrahydro-pyran-4-yl ester

To a solution of 133 g (1.31 mol) of tetrahydro-pyran-4-ol in pyridine (1.5 L) are added 373 g (1.95 mol) of p-toluene-sulfonylchloride portionwise at 10° C. After complete addition the reaction is allowed to warm to room temperature and stirred for 18 h. The reaction is poured onto a stirred mixture of aqueous HCl/ice. The resulting precipitate is isolated by filtration and dissolved in DCM (1 L). The organic layer is washed with 1M aqueous HCl solution (1 L), followed by saturated aqueous NaHCO₃ solution (1 L) and is then dried over Na₂SO₄. Filtration and concentration of the filtrate under reduced pressure gives 300 g of toluene-4-sulfonic acid tetrahydro-pyran-4-yl ester as an orange oil. Yield: 90%, ES-MS: m/z: 257 [M+H], 279 [M+Na].
¹H-NMR (250 MHz, CHLOROFORM-d) δ ppm 1.66-1.96 (4 H, m), 2.45 (3 H, s), 3.47 (2 H, ddd, J=11.76, 8.19, 3.50 Hz), 3.79-3.95 (2 H, m), 4.69 (1 H, tt, J=8.13, 4.13 Hz), 7.35 (2 H, d, J=8.07 Hz), 7.76-7.87 (2 H, m)

Step 3: Synthesis of Thioacetic acid S-(tetrahydro-pyran-4-yl)ester

To a solution of 300 g (1.175 mol) of toluene-4-sulfonic acid tetrahydro-pyran-4-yl ester in DMF (3 L) are added 268 g (2.35 mol) potassium thioacetate, followed by a catalytic amount of NaI (0.12 g, 10 mol %) at room temperature. After complete addition, the reaction is heated to 50° C. for 20 h. The reaction mixture is partitioned between TBME (3 L) and water (3 L), the aqueous layer is extracted with TBME (2 L), then saturated with NaCl and extracted again with TBME (2×2 L). The combined organic extracts are dried over $Na_2SO_4$, filtered and the solvent is removed under reduced pressure to afford 153 g of thioacetic acid S-(tetrahydro-pyran-4-yl)ester. Yield: 81%; ES-MS: m/z 161 [M+H]; $^1$H-NMR (250 MHz, CHLOROFORM-d) δ ppm 1.47-1.98 (4 H, m), 2.30 (3 H, s), 3.41-3.74 (3 H, m), 3.88 (2 H, dt, J=11.76, 3.86 Hz)

Step 4: Synthesis of 2-Methyl-2-(tetrahydro-pyran-4-ylsulfanyl)-propionic acid ethyl ester A solution of 153 g (0.96 mol) of thioacetic acid S-(tetrahydro-pyran-4-yl)ester in ethanol (3.5 L) is degassed with nitrogen over 0.5 h and 125 g (2.23 mol) of KOH are added. Then a solution of 250 mL (1.68 mol) of ethyl α-bromoisobutyrate in EtOH (1 L) are added over 0.5 h, during which the temperature is increased to 40° C. The reaction is stirred for 18 h at room temperature under a nitrogen atmosphere. The reaction mixture is filtered, the solid is washed with ethanol (0.5 L) and the filtrate is concentrated under reduced pressure. The crude material is dryloaded onto silica and purified by dry-flash column chromatography (silica, eluent: n-heptanes, 2-10% ethyl acetate) to afford 158 g of 2-methyl-2-(tetrahydro-pyran-4-ylsulfanyl)-propionic acid ethyl ester as an orange-brown oil. Yield: 71%; ES-MS: m/z 233 [M+H]; 1H-NMR
(500 MHz, CHLOROFORM-d) δ ppm 1.28 (3 H, t, J=7.17 Hz), 1.52 (6 H, s), 1.56-1.67 (2 H, m), 1.85 (2 H, dt, J=13.35, 1.64 Hz), 3.04 (1 H, tt, J=10.60, 4.20 Hz), 3.40-3.49 (2 H, m), 3.88 (2 H, dt, J=11.75, 3.81 Hz), 4.14-4.20 (2 H, m)

Step 5: Synthesis of 2-Methyl-2-(tetrahydro-pyran-4-sulfonyl)-propionic acid ethyl ester To a solution of 158 g (0.68 mol) of 2-methyl-2-(tetrahydro-pyran-4-ylsulfanyl)-propionic acid ethyl ester in 1,4-dioxane/water (4/1, 1.6 L) are added 835 g (1.35 mol) of Oxone® in portions over 50 min. The reaction mixture is stirred at room temperature for 18 h. The solid is removed by filtration and washed with 1,4-dioxane (1 L). The combined filtrates are concentrated under reduced pressure. The residue is dissolved in ethyl acetate (1.5 L) and washed with water (1 L). The organic layer is dried over $Na_2SO_4$, filtered and the solvent is removed under reduced pressure to afford 166 g of 2-methyl-2-(tetrahydro-pyran-4-sulfonyl)-propionic acid ethyl ester as a yellow oil. Yield: 92%, ES-MS: m/z 265 [M+H], 287 [M+Na]; $^1$H-NMR (250 MHz, CHLOROFORM-d) δ ppm 1.30 (3 H, t, J=7.08 Hz), 1.65 (6 H, s), 1.89-2.10 (4 H, m), 3.34-3.51 (2 H, m), 3.72-3.90 (1 H, m), 4.06 (2 H, dt, J=11.69, 3.60 Hz), 4.24 (2 H, q, J=7.16 Hz)

Step 6: Synthesis of 2-Methyl-2-(tetrahydro-pyran-4-sulfonyl)-propionic acid

To a solution of 166 g (0.63 mol) of 2-methyl-2-(tetrahydro-pyran-4-sulfonyl)-propionic acid ethyl ester in THF/water (4/1, 1.66 L) are added 50.5 g (1.26 mol) of NaOH pellets in portions over 20 min. The reaction is stirred at room temperature for 2.5 d. The organic solvent is removed under reduced pressure and the aqueous residue is diluted with water (2 L) and washed with DCM (2 L). The aqueous layer is acidified to pH 1-2 with concentrated HCl and then extracted with DCM (3×2 L). The acidic aqueous is further saturated with NaCl and extracted again with DCM (6×2 L). The combined organic extracts are concentrated under reduced pressure to give 123 g of 2-methyl-2-(tetrahydro-pyran-4-sulfonyl)-propionic acid as a white solid. Yield: 83%, ES-MS: m/z 235 [M–H]; $^1$H-NMR (500 MHz, CHLOROFORM-d) δ ppm 1.71 (6 H, s), 1.94-2.12 (4 H, m), 3.47 (2 H, td, J=11.41, 2.98 Hz), 3.73-3.86 (1 H, m), 4.07-4.15 (2 H, m), 6.82 (1 H, br. s.)

Method E

Synthesis of 2-(4-Methanesulfonyl-benzenesulfonyl)-2-methyl-propionic acid

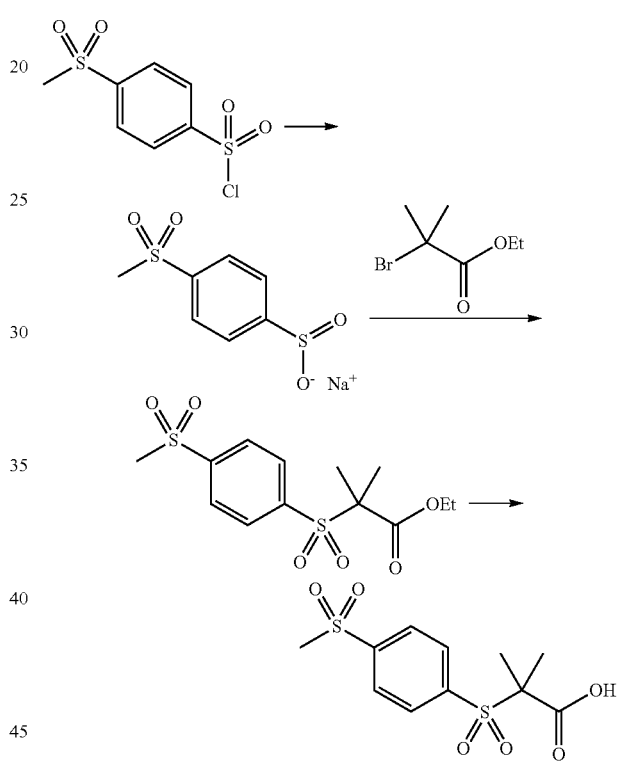

Step 1: Synthesis of Sodium 4-methanesulfonyl-benzenesulfinate

Prepared as described by adaptation of the following references: Faucher, A.-M. et al. *J. Med. Chem.* 2004, 47, 19-21; Binsiti, C. *Eur. J. Med. Chem. Chim. Ther.* 2001, 36, 809-828. Field, L.; Clark, R. D. *Org. Synth.* 1958, 38, 62-64.

To a solution of 0.57 g of $NaHCO_3$ (7.1 mmol) and 1.1 g of $Na_2SO_3$ (8.8 mmol) in water (5.0 mL) were added 1.0 g (3.9 mmol) of 4-methanesulfonyl-benzenesulfonyl chloride. The reaction was heated at 80° C. for 3 h. The solvent was removed under reduced pressure. The filtrate was concentrated under reduced pressure to give sodium 4-methanesulfonyl-benzenesulfinate.

Step 2: Synthesis of 2-(4-Methanesulfonyl-benzenesulfonyl)-2-methyl-propionic acid ethyl ester Prepared as described by adaptation of the following references: Faucher, A.-M. et al. *J. Med. Chem.* 2004, 47, 19-21;

Binsiti, C. *Eur. J. Med. Chem. Chim. Ther.* 2001, 36, 809-828; Field, L.; Clark, R. D. *Org. Synth.* 1958, 38, 62-64; Troeger; Uhde;, *J. Prakt. Chem.* 1899, 59, 320-349.

The crude Sodium 4-methanesulfonyl-benzenesulfinate (3.9 mmol, synthesised by variation A) was suspended in DMF (20 mL). Pyridine (0.6 mL) and ethyl α-bromoisobutyrate (0.7 mL) were added. The reaction was stirred at room temperature under nitrogen for 18 h. The reaction mixture was concentrated under reduced pressure then dissolved with DCM (20 mL) and water (20 mL). The layers were separated and the organic layer was dried over $Na_2SO_4$. Filtration, concentration under reduced pressure, followed by column chromatography (silica, eluent DCM, 0-10% ethyl acetate) afforded 0.67 g of 2-(4-methanesulfonyl-enzenesulfonyl)-2-methyl-propionic acid ethyl ester. (51% yield) $^1$H NMR (400 MHz, $CDCl_3$) ppm 1.25 (3H, t, J=20 Hz), 1.64 (6H, s), 3.11 (3H, s), 4.16 (2H, q, J=18 Hz), 8.07 (2H, d, J=22 Hz), 8.13 (2H, d, J=21 Hz)

Step 3: Synthesis of 2-(4-Methanesulfonyl-benzenesulfonyl)-2-methyl-propionic acid To a solution of 0.67 g (2.07 mmol) of 2-(4-methanesulfonyl-benzenesulfonyl)-2-methyl-propionic acid ethyl ester in THF/water (4/1, 10 mL) were added 100 mg (4.14 mmol) of lithium hydroxide monohydrate. The reaction was stirred at room temperature for 18 h. The reaction was further diluted with water (20 mL) and then washed with DCM (2×15 mL). The basic aqueous layer was cooled in an ice bath and acidified with 1M aqueous HCl solution to pH 2. The acidic aqueous layer was extracted with isopropanol/chloroform (1/1, 3×20 mL). The combined organic extracts were washed with brine, dried over $Na_2SO_4$ and filtered. Concentration of the filtrate under reduced pressure afforded 461 mg of 2-(4-methanesulfonyl-benzenesulfonyl)-2-methyl-propionic acid. (73% yield) $^1$H NMR (400 MHz, DMSO-d6) ppm 1.51 (6H, s), 3.35 (3H, s), 8.08 (2H, d, J=22 Hz), 8.20 (2H, d, J=21 Hz), 13.64 (1H, s)

Amide Method A:

Synthesis of 2-(4-Chloro-benzenesulfonyl)-N-cyclohexyl-2-methyl-propionamide (Example 39, Table 4)

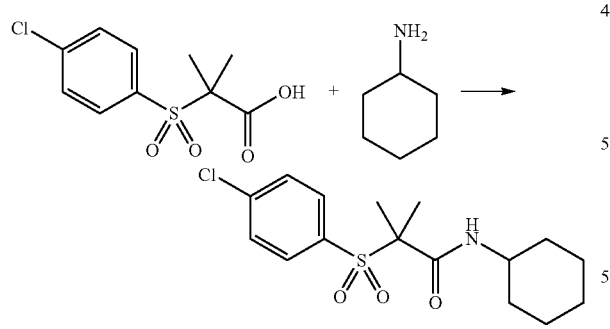

Activation of 26 mg (0.1 mmol) of 2-(4-chloro-benzenesulfonyl)-2-methyl-propionic acid as the corresponding acid chloride is achieved by treatment with thionyl chloride (0.5 mL) at 50° C. for 2 h. The reaction is cooled to room temperature and excess thionyl chloride is removed under reduced pressure.

Cyclohexylamine (15 mg, 0.15 mmol) and N,N,N-triethylamine (41.8 µLs, 0.3 mmol) is dissolved in anhydrous DCM (1.0 mL). The acid chloride (28 mg, 0.1 mmol) is dissolved in DCM (0.5 mL) and is added to the amine solution. The reaction is placed on an orbital shaker for 16 h. The reaction is concentrated. The crude product is dissolved in 10% $H_2O$/DMSO (1 mL). Purification by preparative HPLC provides 2-(4-chloro-benzenesulfonyl)-N-cyclohexyl-2-methyl-propionamide (19 mgs, 0.056 mmol). Yield: 56%; ES-MS: m/z 344.3 [M+H] Compounds in Table 4 amide method A are made according to this procedure.

Amide Method B:

Synthesis of 2-(4-Chloro-benzenesulfonyl)-2-methyl-N-(2-phenylamino-ethyl)-propionamide (Example 19, Table 4)

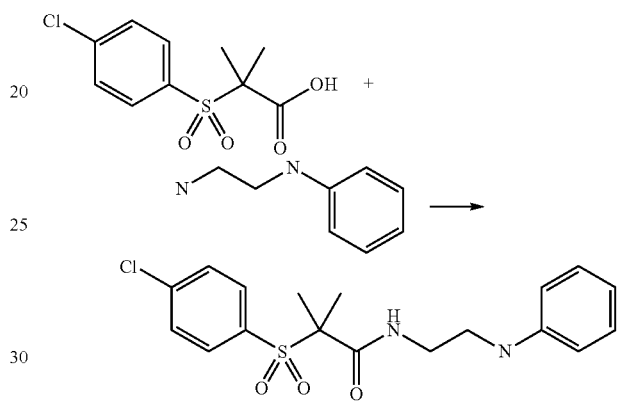

Activation of 100 mg (0.38 mmol) of 2-(4-chloro-benzenesulfonyl)-2-methyl-propionic acid as the corresponding acid chloride is achieved by treatment with thionyl chloride (2 mL) at 80° C. for 2 h. The reaction is cooled to room temperature and excess thionyl chloride is removed under reduced pressure. The crude acid chloride is dissolved in DCM (1 mL) and added dropwise to a solution of N-phenyl-ethylenediamine (52 mg, 0.38 mmol) and N,N-diisopropyl-ethylamine (66 µL, 0.38 mmol) in DCM (1 mL). The reaction is stirred at room temperature for 16 h. The reaction mixture is washed with saturated aqueous $NaHCO_3$ solution. The organic layer is separated, dried ($Na_2SO_4$), filtered and the filtrate is concentrated under reduced pressure. The residue is purified by column chromatography (silica, eluent: DCM, ethyl acetate) to give 110 mg of example 19. Yield: 76%; ES-MS: m/z 381 [M+H]

Compounds in Table 4 amide method B are made according to this procedure.

Amide Method C:

Synthesis of 2-Methyl-N-(2-phenoxy-ethyl)-2-(4-trifluoromethyl-benzenesulfonyl)-propionamide (Example 3, Table 4)

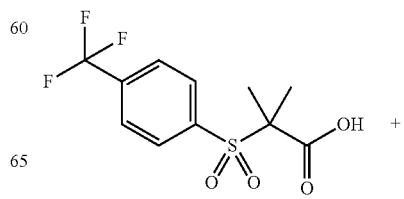

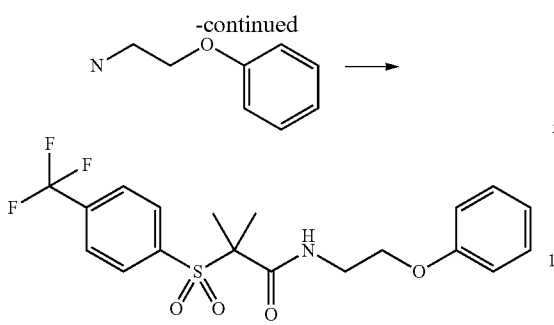

To a solution of 80 mg (0.27 mmol) of 2-methyl-2-(4-trifluoromethyl-benzenesulfonyl)-propionic acid in DCM (4 mL) are added N,N-diisopropylethylamine (56 µL, 0.328 mmol), PS-DCC (506 mg, PolymerLabs, loading 1.6 mmol/g) and DMAP (cat.). The reaction is shaken at room temperature on an orbital shaker for 16 h. The resins are separated by filtration and washed with DCM (5 mL). The filtrate is washed with saturated aqueous NaHCO$_3$ solution. The organic layer is separated, dried (Na$_2$SO$_4$), filtered and the filtrate is concentrated under reduced pressure. The residue is purified by column chromatography (silica, eluent: DCM, ethyl acetate) to give 17 mg of 2-methyl-N-(2-phenoxy-ethyl)-2-(4-trifluoromethyl-benzenesulfonyl)-propionamide. Yield: 15%; ES-MS: m/z 416 [M+H]. Compounds in Table 4 amide method C are made according to this procedure.

Amide Method D

Synthesis of N-(3-tert-Butyl-isoxazol-5-ylmethyl)-2-methyl-2-(tetrahydro-pyran-4-sulfonyl)-propionamide (Example 70, Table 4)

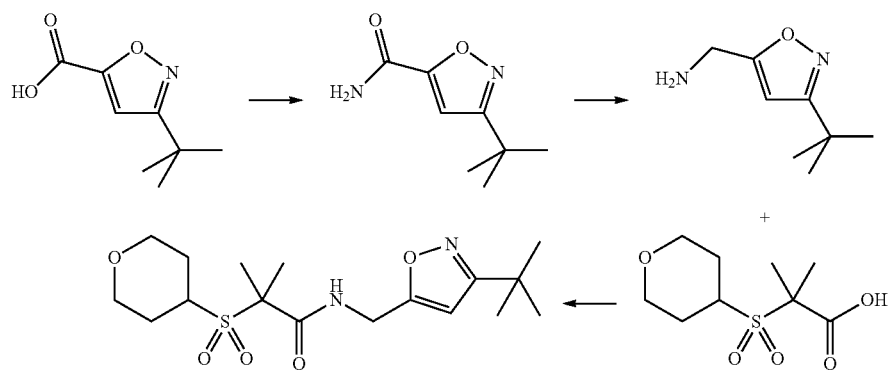

Step 1: Synthesis of 3-tert-Butyl-isoxazole-5-carboxylic acid amide

Activation of 420 mg (2.48 mmol) of 3-tert-butyl-isoxazole-5-carboxylic acid as the corresponding acid chloride is achieved by treatment with oxalyl chloride (0.25 mL, 2.98 mmol) and DMF (1 drop) at room temperature for 18 h. The reaction is concentrated under reduced pressure. The crude acid chloride is dissolved in DCM (1 mL) and added dropwise to a solution of aqueous ammonia (30 wt %, 10 mL,) at 0° C. The reaction is stirred at room temperature for 16 h. The layers are separated and the aqueous phase is extracted with DCM (3×20 mL). The combined organic extracts are dried (MgSO$_4$), filtered and the filtrate is concentrated under reduced pressure to give 334 mg of 3-tert-butyl-isoxazole-5-carboxylic acid amide. Yield: 77%; ES-MS: m/z 169 [M+H]; $^1$H NMR (500 MHz, CHLOROFORM-d) δ ppm 1.36 (9 H, s), 5.75 (1 H, br. s.), 6.46 (1 H, br. s.), 6.89 (1 H, s)

Step 2: Synthesis of (3-tert-butyl-1,2-oxazol-5-yl)methanamine (3-tert-Butyl-1,2-oxazol-5-yl)methanamine is synthesized by adaptation of the following reference: Dannhardt, G.; Kiefer, W.; Lambrecht, G.; Laufer, S.; Mutschler, E.; Schweiger, J.; Striegel, H G. Eur. J. Med. Chem. 1995, 30, 839-850.

To a solution of 220 mg (1.27 mmol) of 3-tert-butyl-isoxazole-5-carboxylic acid amide in anhydrous THF (10 mL) are added 2.54 mL (5.08 mmol, 2M solution in THF) of borane-methylsulfide complex at room temperature under nitrogen atmosphere. The reaction is heated to reflux for 3 h. A further portion of borane-methylsulfide complex (1.3 mL) is added and the reaction is heated for 4 h. The reaction mixture is quenched by addition of methanol and allowed to stand at room temperature for 16 h. The mixture is concentrated under reduced pressure and 1M aqueous HCl solution (8 mL) is added. The mixture is heated to reflux for 1 h, then cooled to 0° C., neutralized by addition of 6M aqueous NaOH solution and solid K$_2$CO$_3$. The mixture is extracted with diethyl ether (5×10 mL) and the combined organic extracts are dried (MgSO4), filtered and the filtrate is concentrated under reduced pressure. The residue is purified twice by column chromatography 9silica, eluent DCM, 0-10% methanol) to afford 84 mg of (3-tert-butyl-1,2-oxazol-5-yl)methanamine. Yield: 34%; ES-MS: m/z 155 [M+H]; $^1$H NMR (250 MHz, CHLOROFORM-d) δ ppm 1.33 (9 H, s), 1.84 (2 H+H$_2$O, br. s.), 3.96 (2 H, s), 6.07 (1 H, s)

Step 3: Synthesis of N-(3-tert-Butyl-isoxazol-5-ylmethyl)-2-methyl-2-(tetrahydro-pyran-4-sulfonyl)-propionamide Activation of 51 mg (0.22 mmol) of 2-methyl-2-(tetrahydro-pyran-4-sulfonyl)-propionic acid as the corresponding acid chloride is achieved by treatment with oxalyl chloride (0.04 mL) and DMF (1 drop) in DCM (2 mL) at room temperature for 1 h. The reaction is concentrated under reduced pressure. The crude acid chloride is dissolved in DCM (1 mL) and added dropwise to a solution of (3-tert-butyl-1,2-oxazol-5-yl)methanamine (42 mg, 80%, 0.22 mmol) and N,N-diisopropylethylamine (114 µL, 0.66 mmol) in DCM (2 mL). The reaction is concentrated under reduced pressure. The residue is purified twice by column chromatography (silica, eluent:

heptanes, 0-50% ethyl acetate then DCM, 20% ethyl acetate), followed by preparative HPLC (neutral method) to give 36 mg of N-(3-tert-butyl-isoxazol-5-ylmethyl)-2-methyl-2-(tetrahydro-pyran-4-sulfonyl)-propionamide. Yield: 44%; ES-MS: m/z 373 [M+H]. Compounds in Table 4 amide method D are made according to this procedure.

TABLE 4

| Example | MOLSTRUCTURE | Acid Method | Amide method | m/z |
|---------|--------------|-------------|--------------|-----|
| 1 | | A | C | 498/500 |
| 2 | | A | C | 432 |
| 3 | | A | C | 416 |
| 4 | | A | C | 349 |
| 5 | | A | B | 378/380 |
| 6 | | A | B | 382/384 |
| 7 | | A | B | 406 |

TABLE 4-continued

| Example | MOLSTRUCTURE | Acid Method | Amide method | m/z |
|---|---|---|---|---|
| 8 | cyclohexyl-SO2-C(CH3)2-C(O)NH-CH2CH2-S-CH2CH3 | A | B | 322 |
| 9 | cyclohexyl-SO2-C(CH3)2-C(O)NH-CH2CH2-O-phenyl | A | B | 354 |
| 10 | cyclohexyl-SO2-C(CH3)2-C(O)NH-CH2CH2-S-C(CH3)3 | A | B | 350 |
| 11 | cyclohexyl-SO2-C(CH3)2-C(O)NH-CH2CH2-S-phenyl | A | B | 370 |
| 12 | 4-Cl-phenyl-SO2-C(CH3)2-C(O)-N(CH3)-CH2CH2-S-phenyl | A | B | 412/414 |
| 13 | 4-CF3-phenyl-SO2-C(cyclobutyl)-C(O)NH-CH2CH2-S-CH2CH3 | A | B | 396 |
| 14 | 4-CF3-phenyl-SO2-C(cyclobutyl)-C(O)NH-CH2CH2-S-C(CH3)3 | A | B | 424 |
| 15 | 3-CF3-phenyl-SO2-C(CH3)2-C(O)NH-CH2CH2-S-C(CH3)3 | A | B | 419 |

TABLE 4-continued

| Example | MOLSTRUCTURE | Acid Method | Amide method | m/z |
|---------|--------------|-------------|--------------|-----|
| 16 | | A | B | 498/500 |
| 17 | | A | B | 393/395 |
| 18 | | A | B | 390/392 |
| 19 | | A | B | 381/383 |
| 20 | | A | B | 415 |
| 21 | | A | B | 382 |
| 22 | | A | B | 365 |
| 23 | | A | B | 412/414 |

TABLE 4-continued

| Example | MOLSTRUCTURE | Acid Method | Amide method | m/z |
|---|---|---|---|---|
| 24 | | A | B | 498/500 |
| 25 | | A | B | 432/434 |
| 26 | | A | B | 374 |
| 27 | | A | B | 392/394 |
| 28 | | A | B | 412/414 |
| 29 | | A | B | 336 |
| 30 | | A | A | 407.2 |

TABLE 4-continued

| Example | MOLSTRUCTURE | Acid Method | Amide method | m/z |
|---------|--------------|-------------|--------------|-----|
| 31 | | A | A | 366.2 |
| 32 | | A | A | 431.2 |
| 33 | | A | A | 331.2 |
| 34 | | A | A | 305.2 |
| 35 | | A | A | 403.2 |
| 36 | | A | A | 441.1 |
| 37 | | A | A | 470.2 |

TABLE 4-continued

| Example | MOLSTRUCTURE | Acid Method | Amide method | m/z |
|---|---|---|---|---|
| 38 | | A | A | 410.1 |
| 39 | | A | A | 344.3 |
| 40 | | A | A | 372.3 |
| 41 | | A | A | 358.3 |
| 42 | | A | A | 358.3 |
| 43 | | A | A | 358.3 |

TABLE 4-continued

| Example | MOLSTRUCTURE | Acid Method | Amide method | m/z |
|---------|--------------|-------------|--------------|-----|
| 44 | | A | A | 386.2/388.2 |
| 45 | | A | A | 380.3 |
| 46 | | A | A | 400.2/402.2 |
| 47 | | A | A | 346.3 |
| 48 | | A | A | 362.3 |

TABLE 4-continued

| Example | MOLSTRUCTURE | Acid Method | Amide method | m/z |
|---|---|---|---|---|
| 49 | | A | A | 372.3 |
| 50 | | A | A | 400.2/402.2 |
| 51 | | A | A | 378.3 |
| 52 | | A | A | 386.3 |
| 53 | | A | A | 426.3 |

TABLE 4-continued

| Example | MOLSTRUCTURE | Acid Method | Amide method | m/z |
|---|---|---|---|---|
| 54 | | A | A | 400.3 |
| 55 | | A | A | 438.2 |
| 56 | | A | A | 432.1/434.1 |
| 57 | | A | A | 376.3 |

TABLE 4-continued

| Example | MOLSTRUCTURE | Acid Method | Amide method | m/z |
|---------|--------------|-------------|--------------|-----|
| 58 | | A | A | 380.2 |
| 59 | | A | A | 434.2 |
| 60 | | A | A | 384.2 |
| 61 | | A | A | 384.2 |
| 62 | | A | A | 372.4 |

TABLE 4-continued

| Example | MOLSTRUCTURE | Acid Method | Amide method | m/z |
|---------|--------------|-------------|--------------|-----|
| 63 | | A | A | 402.2 |
| 64 | | A | A | 396.3 |
| 65 | | A | A | 380.3 |
| 66 | | A | A | 367.3 |
| 67 | | A | A | 418.2/420.2 |

TABLE 4-continued

| Example | MOLSTRUCTURE | Acid Method | Amide method | m/z |
|---|---|---|---|---|
| 68 | | A | A | 434.2/346.2 |
| 69 | | A | A | 354.4 |
| 70 | | D | D | 373 |
| 71 | | C | D | 399 |

Assessment of Biological Properties

The biological properties of the compounds of the formula I are assessed using the assays described below.

A. Human CB1 and CB2 Receptor Binding:

Experimental Method:

CB2 membranes are purchased and made from HEK293 EBNA cells stably transfected with human CB2 receptor cDNA (Perkin Elmer Life and Analytical Sciences). CB1 membranes are isolated from HEK cells stably co-transfected with human CB1 receptor and Gα16 cDNA's. The membrane preparation is bound to scintillation beads (Ysi-Poly-L-lysine SPA beads, GE Healthcare) for 4 h at room temperature in assay buffer containing 50 mM Tris, pH 7.5, 2.5 mM EDTA, 5 mM MgCl$_2$, 0.8% fatty acid free Bovine Serum Albumin. Unbound membrane is removed by washing in assay buffer. Membrane-bead mixture is added to 96-well assay plates in the amounts of 15 ug membrane per well (CB2) or 2.5 ug per well (CB1) and 1 mg SPA bead per well. Compounds are added to the membrane-bead mixture in dose-response concentrations ranging from $1 \times 10^{-5}$ M to $1 \times 10^{-10}$ M with 0.25% DMSO, final. The competition reaction is initiated with the addition of $^3$H-CP55940 (Perkin Elmer Life and Analytical Sciences) at a final concentration of 1.5 nM (CB2) or 2.5 nM (CB1). The reaction is incubated at room temperature for 18 h and read on TopCount NXT plate reader. Total and non-specific binding is determined in the absence and presence of 1.25 uM Win 55212 (Sigma). IC50 values for each compound are calculated as the concentration of compound that inhibits the specific binding of the radioactively labeled ligand to the receptor by 50% using the XLFit 4.1 four parameter logistic model. IC50 values are converted to inhibition constant (Ki) values using Cheng-Prusoff equation.

B. CB2R Mediated Modulation of cAMP Synthesis:

Compounds of the invention are evaluated for their CB2 agonist or inverse agonistic activity in accordance with the following experimental method. Compounds which are shown to bind to CB2 by the binding assay described above but which are not shown to exhibit CB2R-mediated modulation of cAMP synthesis by this assay are presumed to be CB2 antagonists.

Experimental Method:

CHO cells expressing human CB2R (Euroscreen) are plated at a density of 5000 cells per well in 384 well plates and incubated overnight at 37° C. After removing the media, the cells are treated with test compounds diluted in stimulation buffer containing 1 mM IBMX, 0.25% BSA and 10 uM Forskolin. The assay is incubated for 30 minutes at 37° C. Cells are lysed and the cAMP concentration is measured using DiscoverX-XS cAMP kit, following the manufacturer's protocol. In this setting, agonists will decrease forskolin induced production of cAMP while inverse agonists will further increase forskolin induced production of cAMP. EC50 of agonists are calculated as follows. The maximal amount of cAMP produced by forskolin compared to the level of cAMP inhibited by 1 uM CP55940 is defined as 100%. The EC50 value of each test compound is determined as the concentration at which 50% of the forskolin-stimulated cAMP synthesis is inhibited. Data is analyzed using a four-parameter logistic model. (Model 205 of XLfit 4.0).

C. CB1R Mediated Modulation of cAMP Synthesis:

Compounds of the invention are evaluated for their CB1 agonist or inverse agonistic activity in accordance with the following experimental method. Compounds which are shown to bind to CB1 by the binding assay described above but which are not shown to exhibit CB1R-mediated modulation of cAMP synthesis by this assay are presumed to be CB1 antagonists.

Experimental Method:

CHO cells expressing human CB1R (Euroscreen) are plated at a density of 5000 cells per well in 384 well plates and incubated overnight at 37° C. After removing the media, the cells are treated with test compounds diluted in stimulation buffer containing 1 mM IBMX, 0.25% BSA and 10 uM Forskolin. The assay is incubated for 30 minutes at 37° C. Cells are lysed and the cAMP concentration is measured using DiscoverX-XS cAMP kit, following the manufacturer's protocol. In this setting, agonists will decrease forskolin induced production of cAMP while inverse agonists will further increase forskolin induced production of cAMP. EC50 of agonists are calculated as follows. The maximal amount of cAMP produced by forskolin compared to the level of cAMP inhibited by 1 uM CP55940 is defined as 100%. The EC50 value of each test compound is determined as the concentration at which 50% of the forskolin-stimulated cAMP synthesis is inhibited. Data is analyzed using a four-parameter logistic model. (Model 205 of XLfit 4.0).

Compounds Having Agonist Activity

Through the use of the above described assays compounds are found to exhibit agonist activity and thus to be particularly well suited for the treatment of pain as well as for the treatment of inflammation. Preferred compounds of the invention will have an activity range of CB2 (<500 nM).

Therapeutic Use

As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist, antagonist and inverse agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; extensive metastases,;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.

(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;

(xxii) Cancer pain induced by or associated with tumors such as lymphatic leukemia; Hodgkin's disease, malignant lymphoma; lymphogranulomatoses; lympho sarcoma; solid malignant tumors; extensive metastases;

(xxiii) Headache such as cluster headache, migraine with and without aura, tension type headache, headache with different origins, headache disorders including prophylactic and acute use;

(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritus, vitiligo, general gastrointestinal disorders, disturbances of visceral motility at respiratory, genitourinary, gastrointestinal or vascular regions, wounds, burns, tissue damage and postoperative fever, syndromes associated with Itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for Example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical As s' n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

The invention claimed is:
1. A compound of the formula (I)

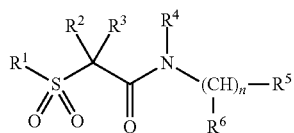

(I)

wherein:
$R^1$ is phenyl wherein each $R^1$ is optionally substituted with 1-3 substituents chosen from $C_{1-4}$ alkyl group substituted with 1-3 halogens, or from $C_{3-10}$ cycloalkyl, $C_{1-4}$ alkoxy, $C_{1-4}$ alkylsulfonyl, acyl, cyano, hydroxyl and halogen;
$R^2$ and $R^3$ are $C_{1-4}$ alkyl or hydrogen with the proviso that both $R^2$ and $R^3$ cannot be hydrogen;
$R^4$ is hydrogen or methyl;
$R^5$ is phenyl wherein each $R^5$ is optionally substituted with 1-3 substituents chosen from $C_{1-4}$ alkyl group optionally substituted with 1-3 halogens, $C_{1-4}$ alkoxy, acyl, —C(O)-heteroaryl, cyano, hydroxyl and halogen;
$R^6$ is hydrogen or $C_{1-4}$ alkyl;
n is 1, 2, 3 or 4;
wherein any carbon atom on the formula (I) or any R substituent listed above is optionally partially or fully halogenated where possible;
or a pharmaceutically acceptable salt thereof.

2. The compound according to claim 1, and wherein
$R^1$ is phenyl, optionally substituted with 1-3 substituents chosen from $C_{1-4}$ alkyl group substituted with 1-3 halogens, or from $C_{1-4}$ alkoxy, $C_{1-4}$ alkylsulfonyl, acyl, cyano, hydroxyl and halogen;
$R^2$ and $R^3$ are independently methyl, ethyl, n-propyl, isopropyl, t-Bu, or hydrogen with the proviso that both $R^2$ and $R^3$ cannot be hydrogen;
$R^4$ is hydrogen or methyl;
$R^5$ is phenyl, optionally substituted with 1-3 substituents chosen from $C_{1-4}$ alkyl group optionally substituted with 1-3 halogens, $C_{1-4}$ alkoxy, acyl, —C(O)-heteroaryl, cyano, hydroxyl and halogen;
$R^6$ is hydrogen or $C_{1-3}$ alkyl.

3. The compound according to claim 2, and wherein
$R^1$ is phenyl, optionally substituted with 1-3 substituents chosen from $C_{1-4}$ alkyl group substituted with 1-3 halogens, or from $C_{1-4}$ alkoxy, $C_{1-4}$ alkylsulfonyl, and halogen.

4. The compound according to claim 3, and wherein
$R^2$ and $R^3$ are independently methyl.

5. The compound according to claim 4, and wherein
$R^4$ is hydrogen or methyl;
$R^5$ is phenyl, optionally substituted with 1-3 substituents chosen from $C_{1-4}$ alkyl group optionally substituted with 1-3 halogens, $C_{1-4}$ alkoxy, acyl, and halogen.

6. The compound according to claim 2, and wherein
$R^1$ is phenyl, optionally substituted with 1-3 substituents chosen from $C_{1-4}$ alkyl group substituted with 1-3 halogens, or from $C_{1-4}$ alkoxy, $C_{1-4}$ alkylsulfonyl, and halogen;
$R^2$ and $R^3$ are independently methyl;
$R^5$ is phenyl, optionally substituted with 1-3 substituents chosen from $C_{1-4}$ alkyl group optionally substituted with 1-3 halogens, $C_{1-4}$ alkoxy, acyl, and halogen;
$R^6$ is hydrogen or methyl;
n is 1, 2 or 3.

7. The compound according to claim 6, and wherein
$R^1$ is phenyl, optionally substituted with 1-2 substituents chosen from trifluoromethyl, and chloro;
$R^2$ and $R^3$ are methyl;
$R^4$ is hydrogen;
$R^5$ is phenyl, optionally substituted with 1-3 substituents chosen from $C_{1-4}$ alkyl, trifluoromethyl, $C_{1-4}$ alkoxy, fluoro and chloro.

8. The compound according to claim 7, and wherein
$R^1$ is phenyl optionally substituted by a substituent chosen from trifluoromethyl, and chloro;
$R^2$ and $R^3$ are methyl;
$R^5$ is phenyl, optionally substituted with 1-3 substituents chosen from $C_{1-4}$ alkyl, trifluoromethyl, methoxy, fluoro and chloro;
n is 2.

9. The compound according to claim 1, and wherein
$R^2$ and $R^3$ are methyl.

10. A compound of the formula (IA)

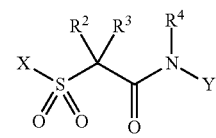

(IA)

wherein

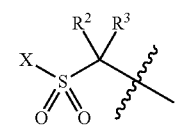

of the formula (IA) is chosen from any of A1-A16 in Table I, and

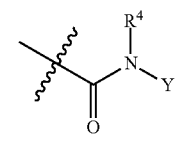

of the formula (IA) is chosen from any of B1-B15 in Table I,

TABLE I

TABLE I-continued
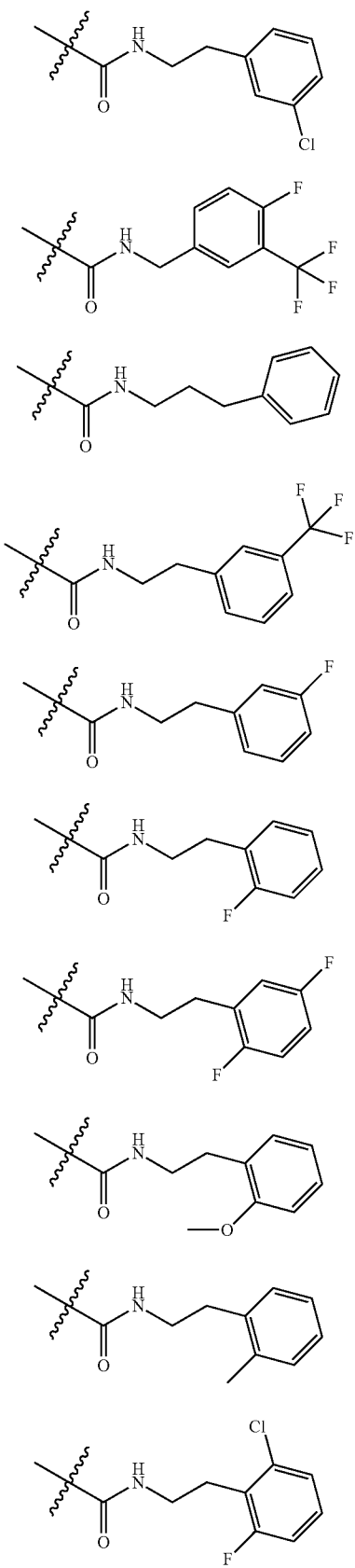
TABLE I-continued
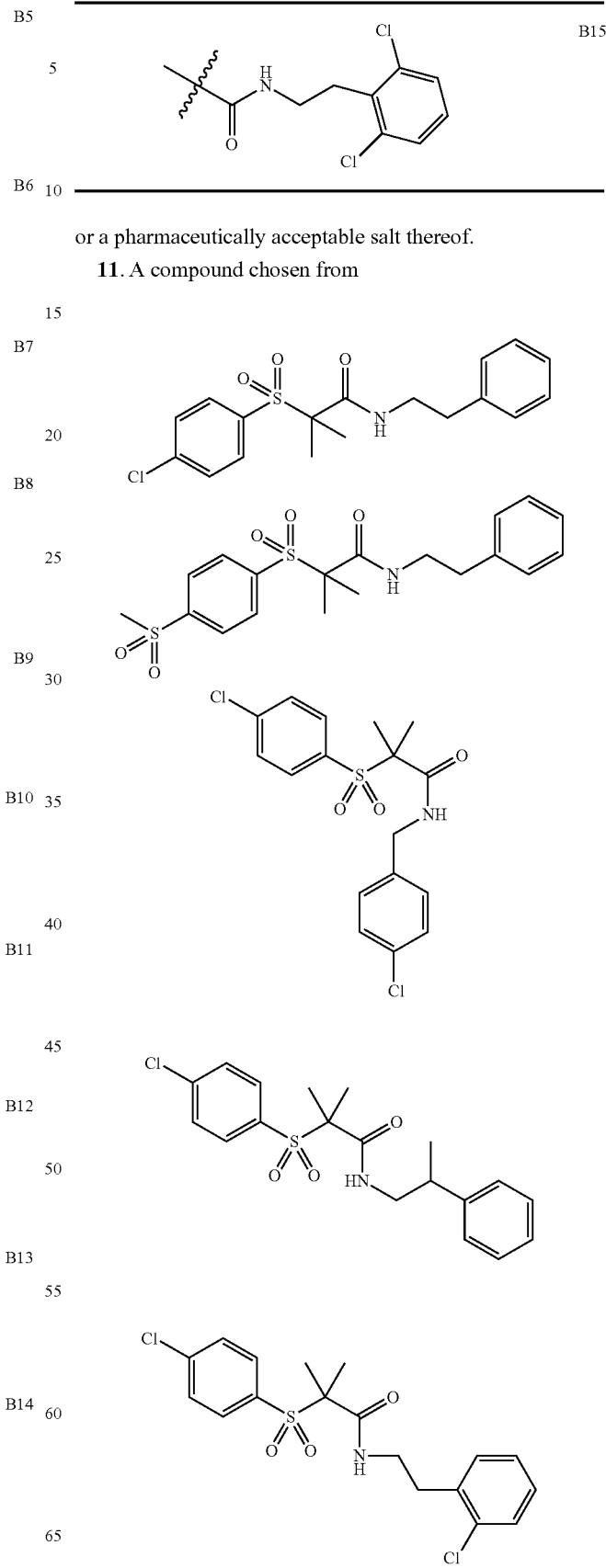
or a pharmaceutically acceptable salt thereof.
11. A compound chosen from

87
-continued
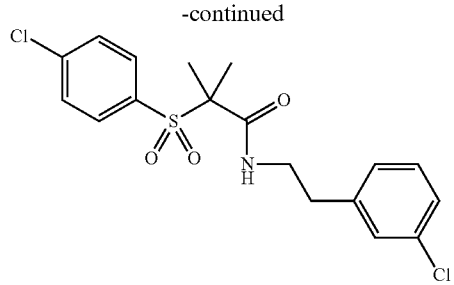
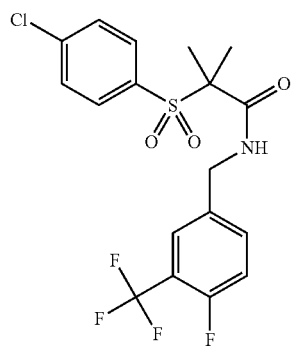 [SMILES: CC(C)(C(=O)NCc1ccc(F)c(C(F)(F)F)c1)S(=O)(=O)c1ccc(Cl)cc1]
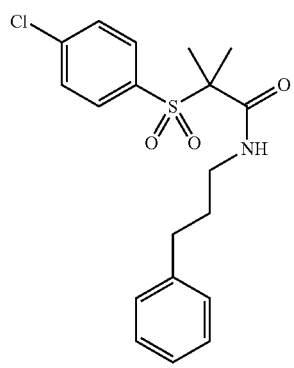 [SMILES: CC(C)(C(=O)NCCCc1ccccc1)S(=O)(=O)c1ccc(Cl)cc1]
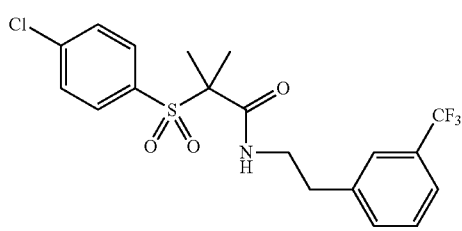 [SMILES: CC(C)(C(=O)NCCc1cccc(C(F)(F)F)c1)S(=O)(=O)c1ccc(Cl)cc1]
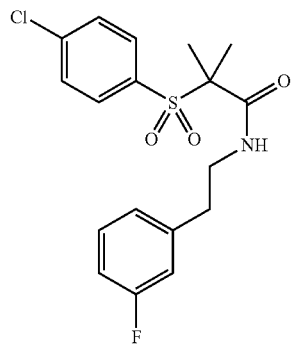 [SMILES: CC(C)(C(=O)NCCc1cccc(F)c1)S(=O)(=O)c1ccc(Cl)cc1]
88
-continued
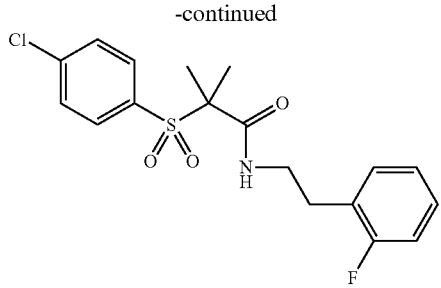
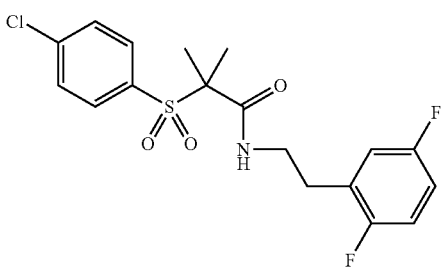
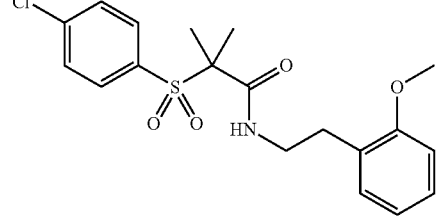
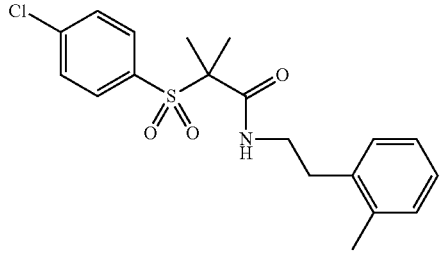 [SMILES: Cc1ccccc1CCNC(=O)C(C)(C)S(=O)(=O)c1ccc(Cl)cc1]
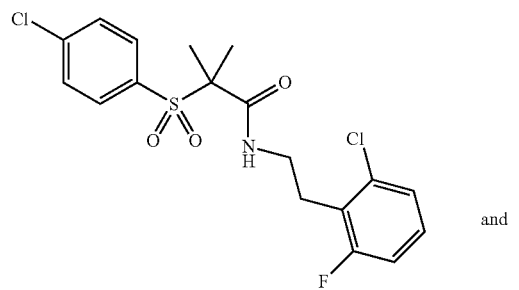
and
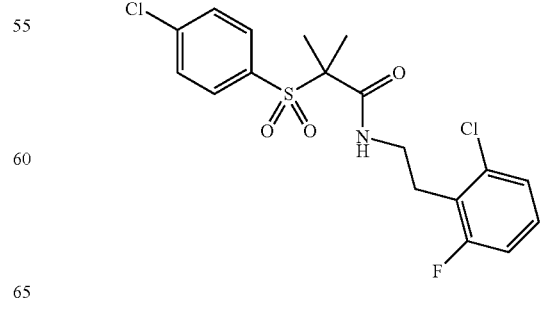
or a pharmaceutically acceptable salt thereof.

12. A pharmaceutical composition comprising a therapeutically effective amount of a compound according to claim 1 and one or more pharmaceutically acceptable carriers and/or adjuvants.

* * * * *